United States Patent
Tadege et al.

(10) Patent No.: US 9,074,216 B2
(45) Date of Patent: Jul. 7, 2015

(54) METHODS AND COMPOSITIONS FOR ALTERING PLANT BIOMASS

(75) Inventors: Million Tadege, Stillwater, OK (US); Kirankumar Mysore, Ardmore, OK (US)

(73) Assignee: The Samuel Roberts Noble Foundation, Inc., Ardmore, OK (US)

(*) Notice: Subject to any disclaimer, the term of this patent is extended or adjusted under 35 U.S.C. 154(b) by 884 days.

(21) Appl. No.: 12/635,603

(22) Filed: Dec. 10, 2009

(65) Prior Publication Data

US 2010/0146670 A1    Jun. 10, 2010

Related U.S. Application Data

(60) Provisional application No. 61/121,479, filed on Dec. 10, 2008.

(51) Int. Cl.
*C12N 15/82* (2006.01)
*C07K 14/415* (2006.01)

(52) U.S. Cl.
CPC ........ *C12N 15/8261* (2013.01); *C12N 15/8225* (2013.01); *C12N 15/82* (2013.01); *C12N 15/8201* (2013.01); *C12N 15/8241* (2013.01); *C07K 14/415* (2013.01)

(58) Field of Classification Search
None
See application file for complete search history.

(56) References Cited

U.S. PATENT DOCUMENTS 7,196,245 B2 *    3/2007    Jiang et al. ............... 800/278

OTHER PUBLICATIONS

Dai et al (2007, Plant Physiology 144:380-390).*
Bowie et al, Science 247:1306-1310, 1990.*
McConnell et al, Nature 411 (6838):709-713, 2001.*
Tadege et al (2011, The Plant Cell 23:2125-2142).*
Haecker et al., "Expression dynamics of WOX genes mark cell fate decisions during early embryonic patterning in arabidopsis thaliana," *Development*, 131:657-668, 2004.
Matsumoto et al., "A homeobox gene, pressed flower, regulates lateral axis-dependent development of *Arabidopsis* flowers," *Genes Devel.*, 15:3355-3364, 2004.
Nardmann et al., "The maize duplicate genes narrow sheath1 and narrow sheath2 encode a conserved homeobox gene function in a lateral domain of shoot apical meristems," *Development*, 131:2827-2839, 2004.
Tadege et al., "Large-scale insertional mutagenesis using the Tnt1 retrotransposon in the model legume *M. truncatula truncatula*," *Plant J.*, 54:335-347, 2008.
Tadege et al., "Development of Tnt1-insertion mutants in *Medicago truncatula* for efficient forward and reverse screens," IV International Legume Genetics and Genomics Conference, Puerto Vallarta, Mexico, Dec. 7-12, 2008.
Tadege et al., "Insertional mutagenesis: a Swiss army knife for functional genomics of *M. truncatula truncatula*," *Trends in Plant Sci.*, 10:229-235, 2005.
Tadege et al., "Mutagenesis and beyond! Tools for understanding legume biology," *Plant Physiology*, 151:978-984, 2009.
Tauro et al., "Germination, field establishment patterns and nitrogen fixation of indigenous legumes on nutrient-depleted soils," *Symbiosis*, 48:92-101, 2009.
Udvardi et al., "Functional genomics of nitrogen fixation," IV International Legume Genetics and Genomics Conference, Puerto Vallarta, Mexico, Dec. 7-12, 2008.
Wang et al., "Control of compound leaf development by *Medicato truncatula* FLO/LFY ortholog single leaflet1 (SGL1)," *Plant Physiol.*, 146:1759-1772, 2008.

* cited by examiner

*Primary Examiner* — Stuart F Baum
(74) *Attorney, Agent, or Firm* — Dentons US LLP

(57) ABSTRACT

The invention provides coding and promoter sequences for an STF gene, which affects lamina expansion in plants. Vectors, transgenic plants, seeds, and host cells comprising a heterologous STF gene are also provided. Additionally provided are methods of altering biomass in a plant using the STF gene.

24 Claims, 13 Drawing Sheets

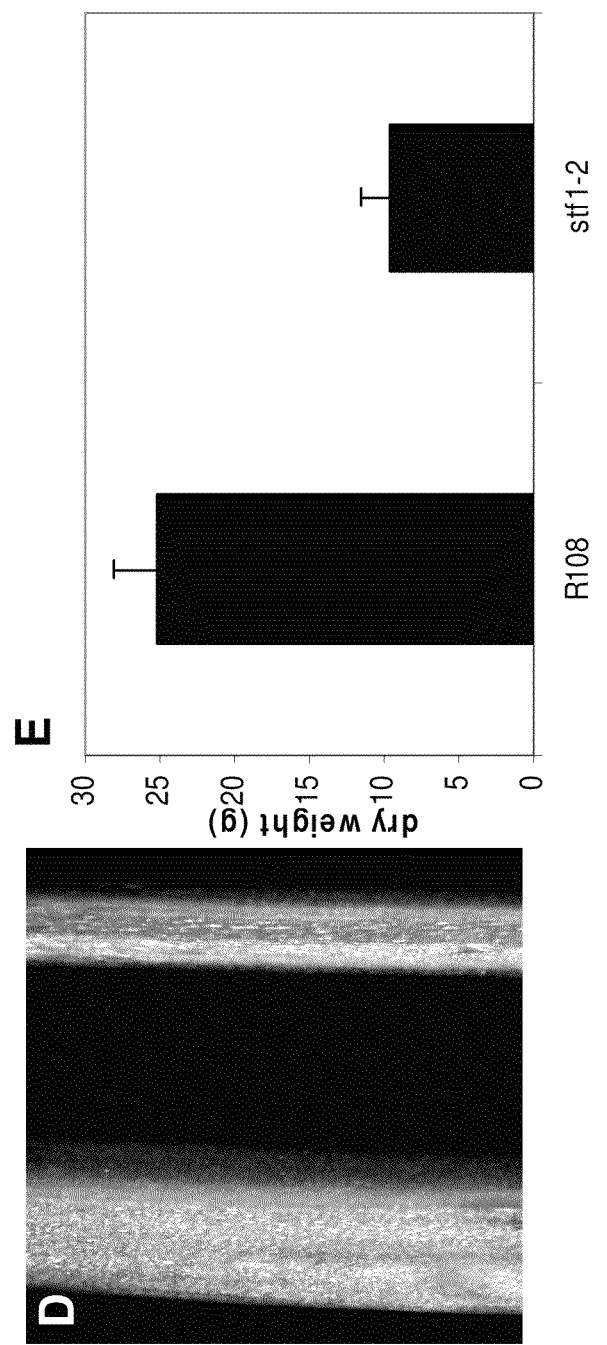
FIG. 1 (Contd.)

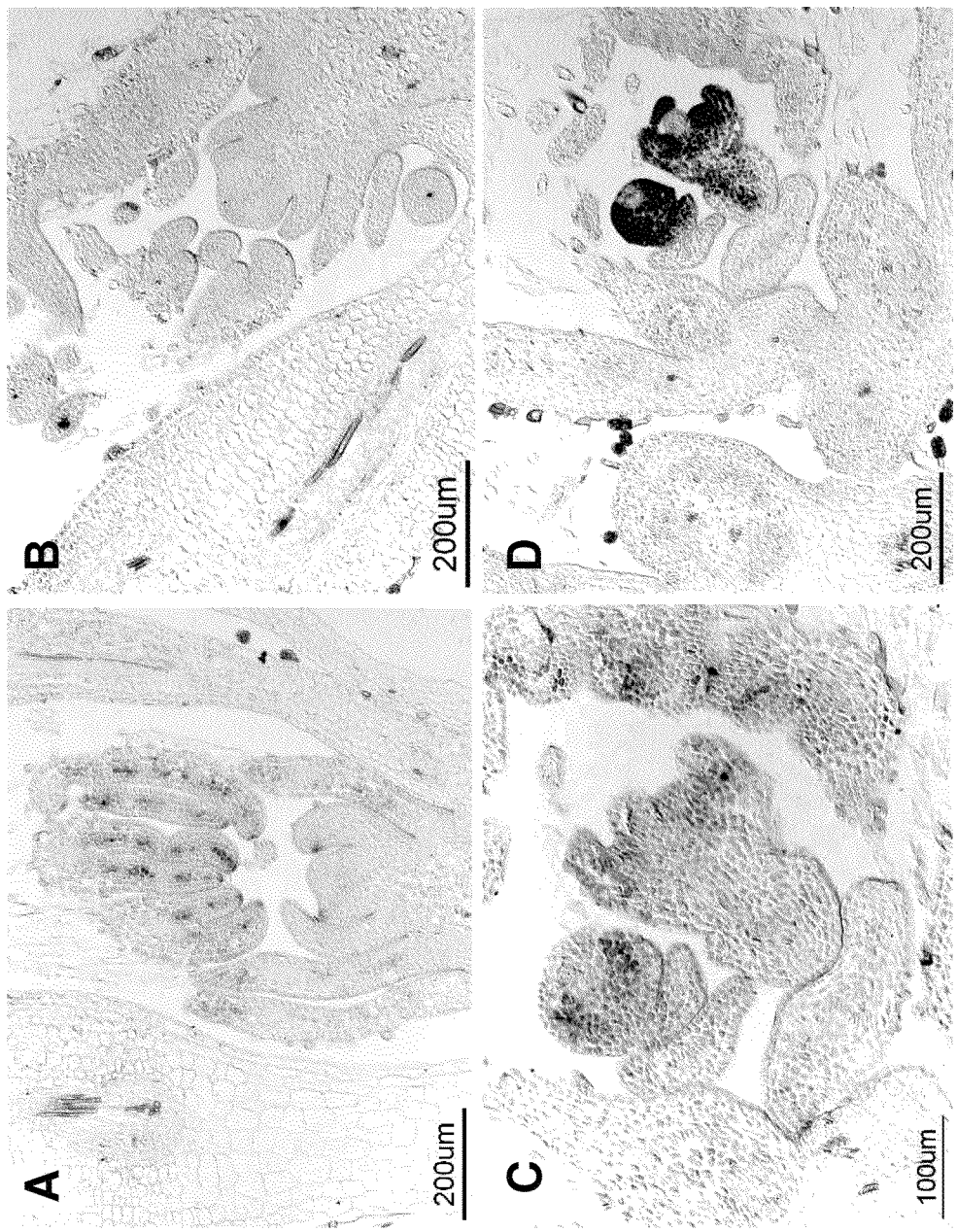

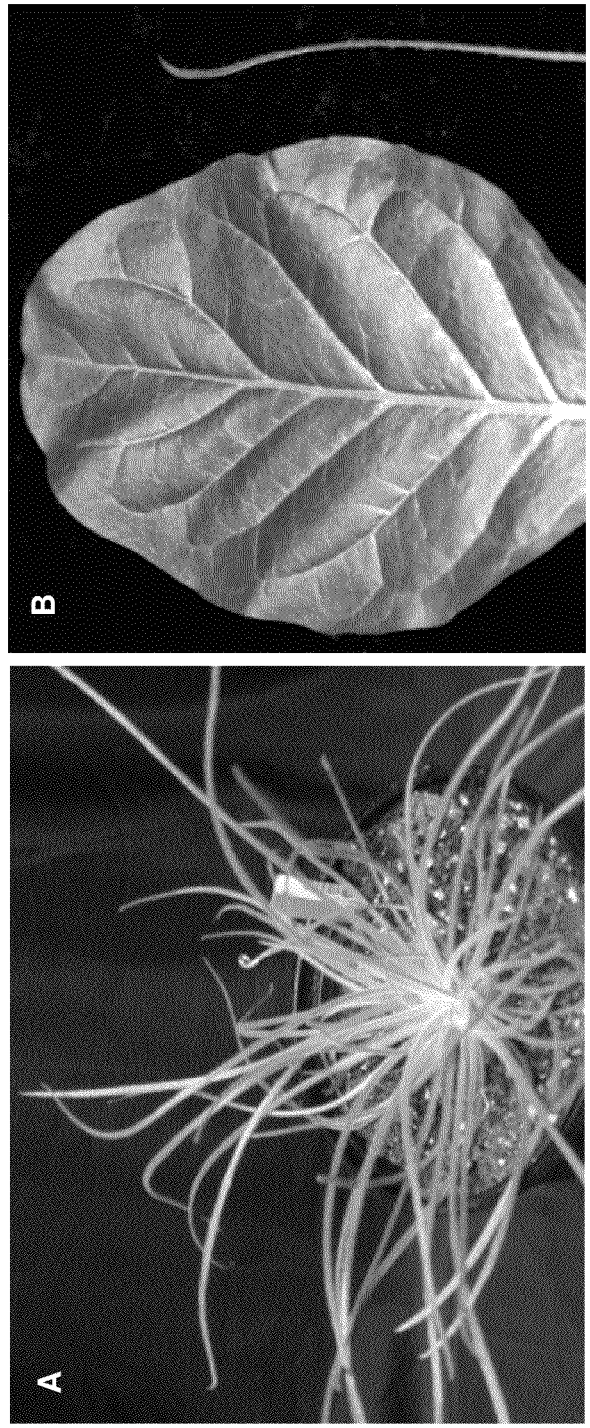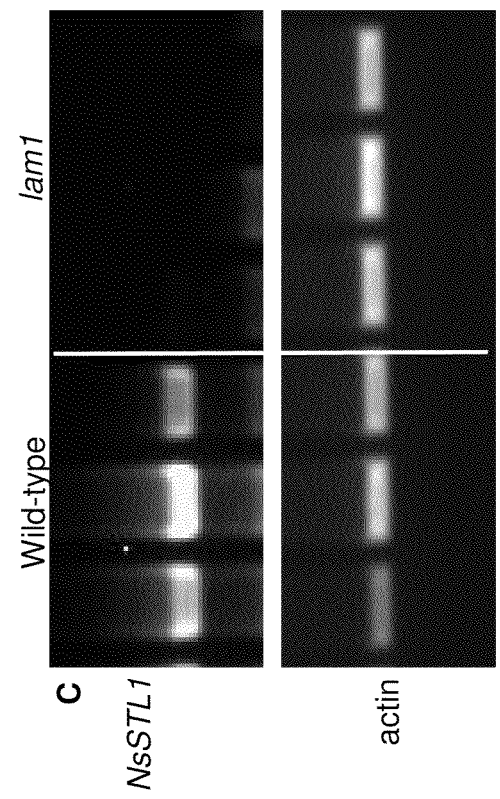
FIG. 8

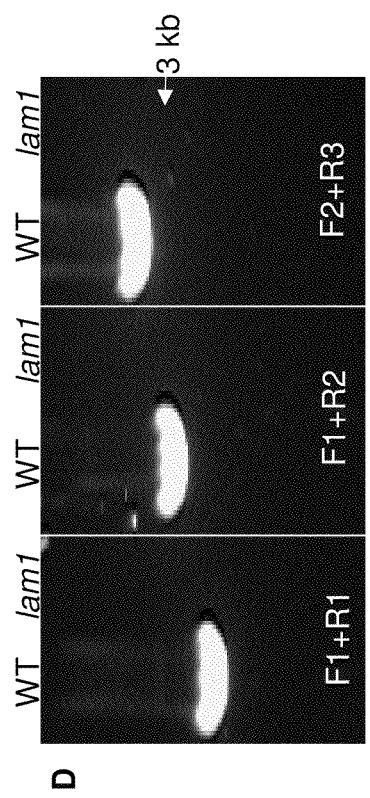
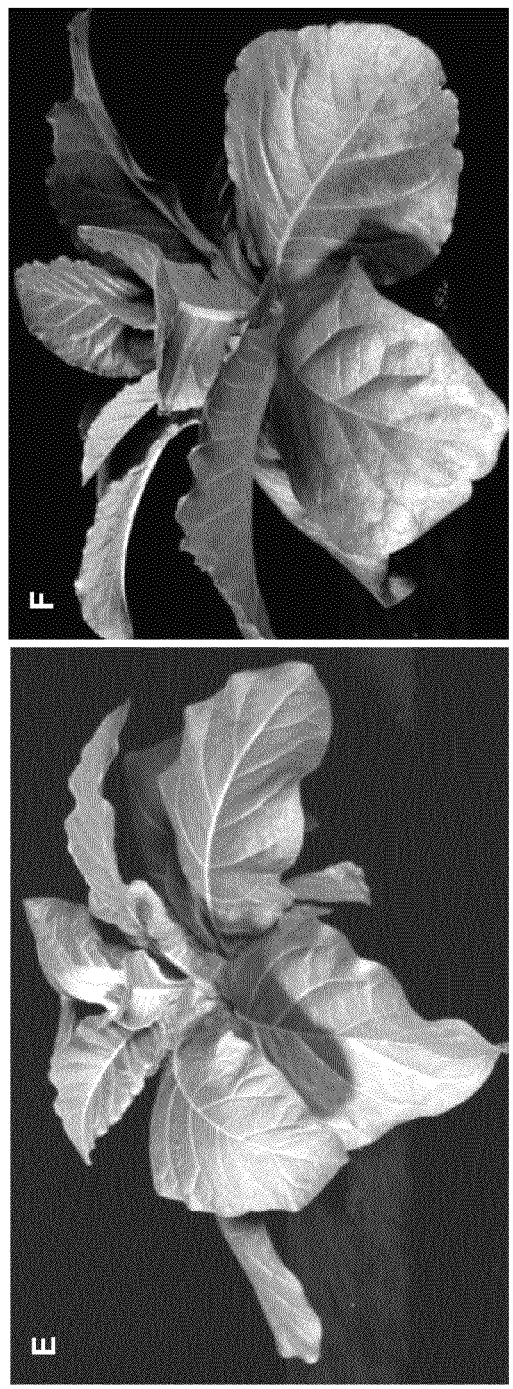
FIG. 8 (Contd.)

SEQUENCE LISTING

```
<160> NUMBER OF SEQ ID NOS: 29

<210> SEQ ID NO 1
<211> LENGTH: 1077
<212> TYPE: DNA
<213> ORGANISM: Medicago truncatula

<400> SEQUENCE: 1
atgtggatgg tgggttacaa tgaaggtggt gagttcaaca tggctgatta tccattcagt      60
ggaaggaaac taaggcctct cattccaaga ccagtcccag tcctactac ttctcctaac     120 agcacttcaa ctataactcc ttccttaaac cgcattcatg gtggcaatga tttattttca     180
caatatcatc acaatctgca gcagcaagca tcagtaggag atcatagcaa gagatcagag     240
ttgaataata ataataatcc atctgcagca gttgtggtga gttcaagatg gaatccaaca     300
ccagaacagt taagagcact ggaagaattg tatagaagag gaacaagaac accttctgct     360
gagcaaatcc aacaaataac tgcccagctt agaaaatttg gaaaaattga aggcaaaaat     420
gttttctatt ggtttcagaa tcacaaagcc agagaaaggc aaaaacgacg gcgtcaaatg     480
gaatcagcag ctgctgagtt tgattctgct attgaaaaga aagacttagg cgcaagtagg     540
acagtgtttg aagttgaaca cactaaaaac tggctaccat ctacaaattc cagtaccagt     600
actcttcatc ttgcagagga atctgtttca attcaaaggt cagcagcagc aaaagcagat     660
ggatggctcc aattcgatga agcagaatta cagcaaagaa gaaactttat ggaaaggaat     720
gccacgtggc atatgatgca gttaacttct tcttgtccta cagctagcat gtccaccaca     780
accacagtaa caactagact tatggaccca aaactcatca agacccatga actcaactta     840
ttcatttcac ctcacacata caagaaaga gaaaacgctt ttatccactt aaatactagt     900
agtactcatc aaaatgaatc tgatcaaacc cttcaacttt tcccaataag gaatggagat     960
catggatgca ctgatcatca tcatcatcat cataacatta tcaaagagac acagatatca    1020
gcttcagcaa tcaatgcacc caaccagttt attgagtttc ttcccttgaa aaactga      1077

<210> SEQ ID NO 2
<211> LENGTH: 358
<212> TYPE: PRT
<213> ORGANISM: Medicago truncatula
```

```
<400> SEQUENCE: 2

Met Trp Met Val Gly Tyr Asn Glu Gly Glu Phe Asn Met Ala Asp
1               5                   10                  15

Tyr Pro Phe Ser Gly Arg Lys Leu Arg Pro Leu Ile Pro Arg Pro Val
                20                  25                  30

Pro Val Pro Thr Thr Ser Pro Asn Ser Thr Ser Thr Ile Thr Pro Ser
                35                  40                  45

Leu Asn Arg Ile His Gly Gly Asn Asp Leu Phe Ser Gln Tyr His His
    50                  55                  60

Asn Leu Gln Gln Gln Ala Ser Val Gly Asp His Ser Lys Arg Ser Glu
65                  70                  75                  80

Leu Asn Asn Asn Asn Pro Ser Ala Ala Val Val Ser Ser Arg
                85                  90                  95

Trp Asn Pro Thr Pro Glu Gln Leu Arg Ala Leu Glu Glu Leu Tyr Arg
                100                 105                 110

Arg Gly Thr Arg Thr Pro Ser Ala Glu Gln Ile Gln Gln Ile Thr Ala
                115                 120                 125

Gln Leu Arg Lys Phe Gly Lys Ile Glu Gly Lys Asn Val Phe Tyr Trp
130                 135                 140

Phe Gln Asn His Lys Ala Arg Glu Arg Gln Lys Arg Arg Gln Met
145                 150                 155                 160

Glu Ser Ala Ala Ala Glu Phe Asp Ser Ala Ile Glu Lys Lys Asp Leu
                165                 170                 175

Gly Ala Ser Arg Thr Val Phe Glu Val Glu His Thr Lys Asn Trp Leu
                180                 185                 190

Pro Ser Thr Asn Ser Ser Thr Ser Thr Leu His Leu Ala Glu Glu Ser
                195                 200                 205

Val Ser Ile Gln Arg Ser Ala Ala Lys Ala Asp Gly Trp Leu Gln
                210                 215                 220

Phe Asp Glu Ala Glu Leu Gln Gln Arg Asn Phe Met Glu Arg Asn
225                 230                 235                 240

Ala Thr Trp His Met Met Gln Leu Thr Ser Ser Cys Pro Thr Ala Ser
                245                 250                 255

Met Ser Thr Thr Thr Val Thr Thr Arg Leu Met Asp Pro Lys Leu
                260                 265                 270

Ile Lys Thr His Glu Leu Asn Leu Phe Ile Ser Pro His Thr Tyr Lys
                275                 280                 285

Glu Arg Glu Asn Ala Phe Ile His Leu Asn Thr Ser Ser Thr His Gln
290                 295                 300

Asn Glu Ser Asp Gln Thr Leu Gln Leu Phe Pro Ile Arg Asn Gly Asp
305                 310                 315                 320

His Gly Cys Thr Asp His His His His His Asn Ile Ile Lys Glu
                325                 330                 335

Thr Gln Ile Ser Ala Ser Ala Ile Asn Ala Pro Asn Gln Phe Ile Glu
                340                 345                 350

Phe Leu Pro Leu Lys Asn
            355

<210> SEQ ID NO 3
<211> LENGTH: 1023
<212> TYPE: DNA
<213> ORGANISM: Medicago sativa

<400> SEQUENCE: 3
```

```
atggctgatt atccatttgg tggaaggaaa ctaaggcctc tcatgccaag accagtccca    60
gtcccagtcc ctactacttc tcctaacaac acttcaacta taactccttc cttaaaccgc   120
attcatggtg gcaatgattt attttcacaa tatcatcaca atctgcagca gcaaggagat   180
catagcaaga gatcagagtt gaataataat ccagcagcag ttgtggtgag ttcaaggtgg   240
aatccaacac cagaacagtt aagagcactg gaagaattgt atagaagagg aacaagaaca   300
ccttctgctg tacaaatcca acaaatcact gcccagctta gaaagtttgg aaaaattgaa   360
ggcaaaaatg ttttctattg gtttcagaat cacaaagcta gagaaaggca aaacgacgc    420
cgtcaaatgg aatcagctgc tgagtttgat tctgctcttg aaaagaaaga cttaggcgca   480
agtaggacag tgtttgaagt tgaacacacc aaaaactggc taccctctac aaattccagt   540
accagtactc ttcctcttgc aggggaatct gtttcaattc aaaggtcagc agcagcaaaa   600
gcagatggat ggctccaatt cgatgaagca gaattacagc aaagaagaaa ctttatggaa   660
aggaatgcca cgtggcatat gatgcagtta acttcttctt gtcctacagc tagcatgtcc   720
accacaacca cagtaacaac tagacttatg gacccaagac tcatcaagac ccatgaactc   780
aacttattca tttcacctca cacatacaaa gaaagagaaa acgcttttat ccacttaaat   840
actagtagta ctcatcaaaa tgaatctgat caaacccttc aacttttccc aataaggaat   900
ggagatcatg gatgcactga tcatcatcat catcatcata acattatcaa agagacacag   960
atatcagctt cagcaatcaa tgcacccaac cagtttattg agtttcttcc cttgaaaaac  1020
tga                                                                1023
```

<210> SEQ ID NO 4
<211> LENGTH: 353
<212> TYPE: PRT
<213> ORGANISM: Medicago sativa

<400> SEQUENCE: 4

```
Met Trp Met Val Gly Tyr Asn Glu Gly Glu Phe Asn Met Ala Asp
1               5                   10                  15

Tyr Pro Phe Gly Gly Arg Lys Leu Arg Pro Leu Met Pro Arg Pro Val
                20                  25                  30

Pro Val Pro Val Pro Thr Thr Ser Pro Asn Asn Thr Ser Thr Ile Thr
            35                  40                  45

Pro Ser Leu Asn Arg Ile His Gly Gly Asn Asp Leu Phe Ser Gln Tyr
        50                  55                  60

His His Asn Leu Gln Gln Gln Gly Asp His Ser Lys Arg Ser Glu Leu
65                  70                  75                  80

Asn Asn Asn Pro Ala Ala Val Val Ser Ser Arg Trp Asn Pro Thr
                85                  90                  95

Pro Glu Gln Leu Arg Ala Leu Glu Glu Leu Tyr Arg Arg Gly Thr Arg
            100                 105                 110

Thr Pro Ser Ala Val Gln Ile Gln Gln Ile Thr Ala Gln Leu Arg Lys
        115                 120                 125

Phe Gly Lys Ile Glu Gly Lys Asn Val Phe Tyr Trp Phe Gln Asn His
    130                 135                 140

Lys Ala Arg Glu Arg Gln Lys Arg Arg Gln Met Glu Ser Ala Ala
145                 150                 155                 160

Glu Phe Asp Ser Ala Leu Glu Lys Lys Asp Leu Gly Ala Ser Arg Thr
                165                 170                 175

Val Phe Glu Val Glu His Thr Lys Asn Trp Leu Pro Ser Thr Asn Ser
            180                 185                 190
```

```
Ser Thr Ser Thr Leu Pro Leu Ala Gly Glu Ser Val Ser Ile Gln Arg
        195                 200                 205

Ser Ala Ala Lys Ala Asp Gly Trp Leu Gln Phe Asp Glu Ala Glu
    210                 215                 220

Leu Gln Gln Arg Arg Asn Phe Met Glu Arg Asn Ala Thr Trp His Met
225                 230                 235                 240

Met Gln Leu Thr Ser Ser Cys Pro Thr Ala Ser Met Ser Thr Thr Thr
                245                 250                 255

Thr Val Thr Thr Arg Leu Met Asp Pro Arg Leu Ile Lys Thr His Glu
                260                 265                 270

Leu Asn Leu Phe Ile Ser Pro His Thr Tyr Lys Glu Arg Glu Asn Ala
            275                 280                 285

Phe Ile His Leu Asn Thr Ser Ser Thr His Gln Asn Glu Ser Asp Gln
        290                 295                 300

Thr Leu Gln Leu Phe Pro Ile Arg Asn Gly Asp His Gly Cys Thr Asp
305                 310                 315                 320

His His His His His His Asn Ile Ile Lys Glu Thr Gln Ile Ser Ala
                325                 330                 335

Ser Ala Ile Asn Ala Pro Asn Gln Phe Ile Glu Phe Leu Pro Leu Lys
            340                 345                 350

Asn

<210> SEQ ID NO 5
<211> LENGTH: 1107
<212> TYPE: DNA
<213> ORGANISM: Lotus japonicus

<400> SEQUENCE: 5
atgtggatgg tgggttacaa tgaaagtggt gctgaattca acatggctga ttatccattc      60
aatggaagaa aactcaggcc tctcatgcca aggccagtga gtacttctcc aaacaacact     120
aattcaacta caaacaccag tccttgctta agaaccattc atcatggaaa tgatttcttt     180
tcacaatatc agaatctggc atcagtgaca gagcagaaca agagagagtt caacactcca     240
cccgttgtgg tgagctcaag gtggaatcct acaccagaac agctaagggc actggaagaa     300
ttgtacagaa gaggaacaag aacaccatct gcagaacaaa tccagcaaat cacagcacag     360
cttagaaggt ttgggaaaat tgaagggaag aacgttttct attggtttca gaatcacaaa     420
gcaagagaaa ggcagaagcg ccgccgtcaa atggaatcag agctgagggt ccgccccgt     480 gactttgaaa gttctcatca tgacaagaaa gacttaggcg caagtaggac agtgtttgaa     540
gttgaacaga ccaagaacaa ctggccatcc tccacaaact gcactagtac tcttgcagag     600
gaatctgttt caattcaaag tgcagcagca aaagcagtgg ttgctgcaga gtgcagcaga     660
acagatggat ggctccaatt cgatgaaggg gaattacagc agcaaagaag aaactttatg     720
gaaaggaatg ccacgtggcg catgatgcag tttccttgtc ctcctcaacc tccccacttc     780
attaacacac ctcctcaata tgcctctaca actagcatgg ccacagtaac agcagctaga     840
ctcatggacc aaaaactcat taagactcat gcagatctca gcttcttcat ttcacctcac     900
accagagaaa acaacagcat tatccactta agcagtttca ccactgagga taatgttgaa     960
tctcaaaccc ttcaactttt ccccttgcgg aatggagatg gtagcagtga aacagcaat     1020 caacatcaca agagagacag agatatcggtt tcagcaatga atgcaccaag ccagttttt     1080 gagtttctac cattgaagaa gtactga                                        1107
```

<210> SEQ ID NO 6
<211> LENGTH: 368
<212> TYPE: PRT
<213> ORGANISM: Lotus japonicus

<400> SEQUENCE: 6

```
Met Trp Met Val Gly Tyr Asn Glu Ser Gly Ala Glu Phe Asn Met Ala
1               5                   10                  15

Asp Tyr Pro Phe Asn Gly Arg Lys Leu Arg Pro Leu Met Pro Arg Pro
            20                  25                  30

Val Ser Thr Ser Pro Asn Asn Thr Asn Ser Thr Thr Asn Thr Ser Pro
                35                  40                  45

Cys Leu Arg Thr Ile His His Gly Asn Asp Phe Phe Ser Gln Tyr Gln
 50                  55                  60

Asn Leu Ala Ser Val Thr Glu Gln Asn Lys Arg Glu Phe Asn Thr Pro
 65                  70                  75                  80

Pro Val Val Ser Ser Arg Trp Asn Pro Thr Pro Glu Gln Leu Arg
                 85                  90                  95

Ala Leu Glu Glu Leu Tyr Arg Arg Gly Thr Arg Thr Pro Ser Ala Glu
                100                 105                 110

Gln Ile Gln Gln Ile Thr Ala Gln Leu Arg Arg Phe Gly Lys Ile Glu
            115                 120                 125

Gly Lys Asn Val Phe Tyr Trp Phe Gln Asn His Lys Ala Arg Glu Arg
130                 135                 140

Gln Lys Arg Arg Arg Gln Met Glu Ser Glu Ala Glu Gly Pro Pro Arg
145                 150                 155                 160

Asp Phe Glu Ser Ser His His Asp Lys Lys Asp Leu Gly Ala Ser Arg
                165                 170                 175

Thr Val Phe Glu Val Glu Gln Thr Lys Asn Asn Trp Pro Ser Ser Thr
            180                 185                 190

Asn Cys Thr Ser Thr Leu Ala Glu Ser Val Ser Ile Gln Ser Ala
                195                 200                 205

Ala Ala Lys Ala Val Val Ala Ala Glu Cys Ser Arg Thr Asp Gly Trp
210                 215                 220

Leu Gln Phe Asp Glu Gly Glu Leu Gln Gln Arg Arg Asn Phe Met
225                 230                 235                 240

Glu Arg Asn Ala Thr Trp Arg Met Met Gln Phe Pro Cys Pro Pro Gln
                245                 250                 255

Pro Pro His Phe Ile Asn Thr Pro Pro Gln Tyr Ala Ser Thr Thr Ser
            260                 265                 270

Met Ala Thr Val Thr Ala Ala Arg Leu Met Asp Gln Lys Leu Ile Lys
        275                 280                 285

Thr His Ala Asp Leu Ser Phe Ile Ser Pro His Thr Arg Glu Asn
    290                 295                 300

Asn Ser Ile Ile His Leu Ser Ser Phe Thr Thr Glu Asp Asn Val Glu
305                 310                 315                 320

Ser Gln Thr Leu Gln Leu Phe Pro Leu Arg Asn Gly Asp Gly Ser Ser
                325                 330                 335

Glu Asn Ser Asn Gln His His Lys Glu Thr Glu Ile Ser Val Ser Ala
            340                 345                 350

Met Asn Ala Pro Ser Gln Phe Phe Glu Phe Leu Pro Leu Lys Lys Tyr
        355                 360                 365
```

<210> SEQ ID NO 7

<211> LENGTH: 1041
<212> TYPE: DNA
<213> ORGANISM: Glycine max

<400> SEQUENCE: 7

```
atggctgatt atggattcaa tggaggaaaa ctcaggcctc tcatgccaag gccagtgaca    60
tctcctaaca acacttcaaa cacaaactct ccatgcttga gccgcattca tcatggcaac   120
aatttctttt cacaatatca caatctggca tcagtggcag atcagggaaa gagggagttc   180
aaccctccac cagtagtggt gagttcaagg tggaatccaa ccccggagca actgagagca   240
ttggaggaat tgtatagaag agggacaaga acaccatctg cggagcaaat ccaacaaatc   300
acggcacagc ttaggaggtt tggaaaaatt gaagggaaga atgttttcta ttggtttcag   360
aatcacaaag caagagaaag acagaaacgc cgccgtcaaa tggagtcagc tgctgagggt   420
catcacaccc gtgactttga tagtactctt gaaaagaaag acttaggcgc aagtaggaca   480
gtgtttgaag ttgatcagac caagaactgg gcaccctcta caaactgcag tactcttgca   540
gaggaatctg tttcaataca aagggcagca aaagcagcga ttgcagagtg tagaacagat   600
ggatggctcc aattcgatga aggagagtta caacatagaa gaaactttat ggagaggaat   660
gccacgtggc atatgatgca gttatcttgt cctccccctc ctacagtttc accccacctc   720
ataaacacat ctcctattac ctctactact agcatggcca ccgcaaccac agtaacagca   780
agactaatgg acccaaagct cattaagact catgatctca gcttctttac ttcacctaac   840
agagaaaacg gtattatcca cttaagcagt atcagcaccc aggatgataa ttctgtggaa   900
tctcaaaccc ttcaacttt  tccaacaagg aacgcggatc gaagcagtga taacatcaac   960
cagcaaaaag agacagaggt ttcggtttca gcgatgaatg cacccagcca gttttttgag  1020
ttccttccat tgaagaactg a                                            1041
```

<210> SEQ ID NO 8
<211> LENGTH: 346
<212> TYPE: PRT
<213> ORGANISM: Glycine max

<400> SEQUENCE: 8

```
Met Ala Asp Tyr Gly Phe Asn Gly Arg Lys Leu Arg Pro Leu Met Pro
1               5                   10                  15

Arg Pro Val Thr Ser Pro Asn Asn Thr Ser Asn Thr Asn Ser Pro Cys
            20                  25                  30

Leu Ser Arg Ile His His Gly Asn Asn Phe Phe Ser Gln Tyr His Asn
        35                  40                  45

Leu Ala Ser Val Ala Asp Gln Gly Lys Arg Glu Phe Asn Pro Pro Pro
    50                  55                  60

Val Val Val Ser Ser Arg Trp Asn Pro Thr Pro Glu Gln Leu Arg Ala
65                  70                  75                  80

Leu Glu Glu Leu Tyr Arg Arg Gly Thr Arg Thr Pro Ser Ala Glu Gln
                85                  90                  95

Ile Gln Gln Ile Thr Ala Gln Leu Arg Arg Phe Gly Lys Ile Glu Gly
            100                 105                 110

Lys Asn Val Phe Tyr Trp Phe Gln Asn His Lys Ala Arg Glu Arg Gln
        115                 120                 125

Lys Arg Arg Arg Gln Met Glu Ser Ala Ala Glu Gly His His Thr Arg
    130                 135                 140

Asp Phe Asp Ser Thr Leu Glu Lys Lys Asp Leu Gly Ala Ser Arg Thr
145                 150                 155                 160
```

```
Val Phe Glu Val Asp Gln Thr Lys Asn Trp Ala Pro Ser Thr Asn Cys
                165                 170                 175

Ser Thr Leu Ala Glu Glu Ser Val Ser Ile Gln Arg Ala Ala Lys Ala
            180                 185                 190

Ala Ile Ala Glu Cys Arg Thr Asp Gly Trp Leu Gln Phe Asp Glu Gly
        195                 200                 205

Glu Leu Gln His Arg Arg Asn Phe Met Glu Arg Asn Ala Thr Trp His
    210                 215                 220

Met Met Gln Leu Ser Cys Pro Pro Pro Thr Val Ser Pro His Leu
225                 230                 235                 240

Ile Asn Thr Ser Pro Ile Thr Ser Thr Ser Met Ala Thr Ala Thr
                245                 250                 255

Thr Val Thr Ala Arg Leu Met Asp Pro Lys Leu Ile Lys Thr His Asp
            260                 265                 270

Leu Ser Phe Phe Thr Ser Pro Asn Arg Glu Asn Gly Ile Ile His Leu
        275                 280                 285

Ser Ser Ile Ser Thr Gln Asp Asp Asn Ser Val Glu Ser Gln Thr Leu
    290                 295                 300

Gln Leu Phe Pro Thr Arg Asn Ala Asp Arg Ser Ser Asp Asn Ile Asn
305                 310                 315                 320

Gln Gln Lys Glu Thr Glu Val Ser Val Ser Ala Met Asn Ala Pro Ser
                325                 330                 335

Gln Phe Phe Glu Phe Leu Pro Leu Lys Asn
            340                 345

<210> SEQ ID NO 9
<211> LENGTH: 1044
<212> TYPE: DNA
<213> ORGANISM: Vitis vinifera

<400> SEQUENCE: 9
atgtggatga tgggttacaa tgatggggga gagctgaata tgcctgattc attcaatggc      60
aggaagcttc ggcctctgat tccaagacca gctacttcta ccagcggcac tgcaactacc     120
acgtcttctt gtttaagccg catccatggg actgatcttt tggactgaa tcaccatctg     180 gagcaaagca acattagaga gttcaataca actccagtca tagtgagctc acgttggaat     240
ccaaccccgg agcagctaag gaccctagaa gaattatatc ggcgcgggac tcgaacgcct     300
tcggctgagc aaattcagca tatcaccgca cagctccgcc gatacggcaa gattgaaggc     360
aagaatgtgt tttactggtt tcagaaccac aaggcagggg aacggcagaa gcggcgccga     420
caacttgaac cagatgagca gaatcgcgat gttgaaagca cagagaggaa ggaatcagga     480
ggaagtagga caggttttga agaacagacc aagaactggg cactctctac aaactgcagt     540
atacttgcag aggaatctct ttcaatacaa agggcagcaa agcaacagc tgcagcagca     600 gaatgtagaa cagatggatg gatccaattc gatgaagggg aattacagca tagaagaagc     660
ttggtagaaa gaaatgccat tggcagatg atgcagttgt cttgtccttc tccaccacc     720 cacctcataa acacgactac tactacaaga accaaagaag ctgcagcagt tagaagaatg     780
gacccaaagt tcataaagac tcgagatctg aacatcttta tagctcccta cagatcagaa     840
ggtcataatc acttggccgg tgtcggcgcc gatcactcca atgaagaaga gggtggagaa     900
tcccaaaccc ttcagctgtt cccccctccgg agcggcgatg caatgaaaaa cattaatgaa     960
aaagagggcg agatatcagt tgctgccatg aataccaacc tcactcctca ccagtttttt    1020
```

```
gagttccttc cactgaagaa ttaa                                           1044
```

<210> SEQ ID NO 10
<211> LENGTH: 347
<212> TYPE: PRT
<213> ORGANISM: Vitis vinifera

<400> SEQUENCE: 10

| | | | | | | | | | | | | | | |
|---|---|---|---|---|---|---|---|---|---|---|---|---|---|---|
| Met | Trp | Met | Met | Gly | Tyr | Asn | Asp | Gly | Gly | Glu | Leu | Asn | Met | Pro | Asp |
| 1 | | | | 5 | | | | | 10 | | | | | 15 | |
| Ser | Phe | Asn | Gly | Arg | Lys | Leu | Arg | Pro | Leu | Ile | Pro | Arg | Pro | Ala | Thr |
| | | | 20 | | | | | 25 | | | | | 30 | | |
| Ser | Thr | Ser | Gly | Thr | Ala | Thr | Thr | Ser | Ser | Cys | Leu | Ser | Arg | Ile | |
| | | 35 | | | | | 40 | | | | | 45 | | | |
| His | Gly | Thr | Asp | Leu | Phe | Gly | Leu | Asn | His | His | Leu | Glu | Gln | Ser | Asn |
| | 50 | | | | | 55 | | | | | 60 | | | | |
| Ile | Arg | Glu | Phe | Asn | Thr | Thr | Pro | Val | Ile | Val | Ser | Ser | Arg | Trp | Asn |
| 65 | | | | | 70 | | | | | 75 | | | | | 80 |
| Pro | Thr | Pro | Glu | Gln | Leu | Arg | Thr | Leu | Glu | Glu | Leu | Tyr | Arg | Arg | Gly |
| | | | | 85 | | | | | 90 | | | | | 95 | |
| Thr | Arg | Thr | Pro | Ser | Ala | Glu | Gln | Ile | Gln | His | Ile | Thr | Ala | Gln | Leu |
| | | | 100 | | | | | 105 | | | | | 110 | | |
| Arg | Arg | Tyr | Gly | Lys | Ile | Glu | Gly | Lys | Asn | Val | Phe | Tyr | Trp | Phe | Gln |
| | | | 115 | | | | | 120 | | | | | 125 | | |
| Asn | His | Lys | Ala | Arg | Glu | Arg | Gln | Lys | Arg | Arg | Gln | Leu | Glu | Pro | |
| | 130 | | | | | 135 | | | | | 140 | | | | |
| Asp | Glu | Gln | Asn | Arg | Asp | Val | Glu | Ser | Thr | Glu | Arg | Lys | Glu | Ser | Gly |
| 145 | | | | | 150 | | | | | 155 | | | | | 160 |
| Gly | Ser | Arg | Thr | Gly | Phe | Glu | Glu | Gln | Thr | Lys | Asn | Trp | Ala | Leu | Ser |
| | | | | 165 | | | | | 170 | | | | | 175 | |
| Thr | Asn | Cys | Ser | Ile | Leu | Ala | Glu | Glu | Ser | Leu | Ser | Ile | Gln | Arg | Ala |
| | | | 180 | | | | | 185 | | | | | 190 | | |
| Ala | Lys | Ala | Thr | Ala | Ala | Ala | Glu | Cys | Arg | Thr | Asp | Gly | Trp | Ile | |
| | | 195 | | | | | 200 | | | | | 205 | | | |
| Gln | Phe | Asp | Glu | Gly | Glu | Leu | Gln | His | Arg | Arg | Ser | Leu | Val | Glu | Arg |
| | 210 | | | | | 215 | | | | | 220 | | | | |
| Asn | Ala | Ile | Trp | Gln | Met | Met | Gln | Leu | Ser | Cys | Pro | Ser | Pro | Thr | Thr |
| 225 | | | | | 230 | | | | | 235 | | | | | 240 |
| His | Leu | Ile | Asn | Thr | Thr | Thr | Thr | Arg | Thr | Lys | Glu | Ala | Ala | Ala | |
| | | | | 245 | | | | | 250 | | | | | 255 | |
| Val | Arg | Arg | Met | Asp | Pro | Lys | Phe | Ile | Lys | Thr | Arg | Asp | Leu | Asn | Ile |
| | | | 260 | | | | | 265 | | | | | 270 | | |
| Phe | Ile | Ala | Pro | Tyr | Arg | Ser | Glu | Gly | His | Asn | His | Leu | Ala | Gly | Val |
| | | 275 | | | | | 280 | | | | | 285 | | | |
| Gly | Ala | Asp | His | Ser | Asn | Glu | Glu | Gly | Gly | Glu | Ser | Gln | Thr | Leu | |
| | 290 | | | | | 295 | | | | | 300 | | | | |
| Gln | Leu | Phe | Pro | Leu | Arg | Ser | Gly | Asp | Gly | Asn | Glu | Ile | Asn | Glu | |
| 305 | | | | | 310 | | | | | 315 | | | | | 320 |
| Lys | Glu | Gly | Glu | Ile | Ser | Val | Ala | Ala | Met | Asn | Thr | Asn | Leu | Thr | Pro |
| | | | | 325 | | | | | 330 | | | | | 335 | |
| His | Gln | Phe | Phe | Glu | Phe | Leu | Pro | Leu | Lys | Asn | | | | | |
| | | | 340 | | | | | 345 | | | | | | | |

<210> SEQ ID NO 11
<211> LENGTH: 1125

```
<212> TYPE: DNA
<213> ORGANISM: Populus trichocarpa

<400> SEQUENCE: 11
atgtggatga tgggttataa tgatggtggt gaattcaaca tatcagattc tttcaatggc      60
aggaagctta ggccactagt tccaaggcca atacccctcta caaacaacac tccaactgcc    120
tctagtcctc cttgccttgg cagtcgcctt cataacaccg atttctttgc actcaatcag    180
tatcatctgg caagtatggc tgatcaaaac aaaagagaat caacacaca gccagttgta     240
atgagctcaa gatggaatcc aacaccggag cagttaagga cccttgaaga tttgtatcga    300
agagggacta gaacaccctc aactgaccaa attcaagaca taaccgcaca gcttcgtaga    360
tatggaagga ttgaaggaaa gaatgtgttt tactggtttc aaaaccacaa ggcaagagaa    420
aggcaaaagc gtcgacgtca aatggaatct gattcttttg atggtcatct gcaaaatgga    480
catggtattg aaatctttga aggaaagaa tcagaggcaa gtaggacagg ttatgaaggt     540
gaacaaacca gaactgggc tccctctaca aactgcagta cactatcaga ggaatctgtt     600
tcaatatcaa gggcaacaaa aggagcaatg gcagagtact gtagaccaga tggatggatg    660
caactcgatg aaggagaatt acagcataga aggaacttta tagaaaggaa tgccacgtgg    720
gagatgatgc agttgtcttg tccatctccc acccaccaaa gaaacactat ctctagtact    780
agtagcacta caactatgtc aaaacaagga gcagcagcag cgaagctcat taaggctcat    840
gacctcaacg tctttatagc accttacaga gaaaatgggc atcatggagc ccttattaac    900
cagttcaata gcagtgtcat caatgacggg gatgaatcca gaggtggtac tggggaatct    960
caaacccttc aactgtttcc tcttcgtagt ggcggtgacg gcaacaataa tatcgaaagc   1020
attaacgaga gagagagtga ggtatcagtt tctgctgctg aagctttgaa tgctaataac   1080
ttcgctcctt gccagttctt tgagttcctt ccactgaagc actaa                    1125

<210> SEQ ID NO 12
<211> LENGTH: 374
<212> TYPE: PRT
<213> ORGANISM: Populus trichocarpa

<400> SEQUENCE: 12

Met Trp Met Met Gly Tyr Asn Asp Gly Gly Glu Phe Asn Ile Ser Asp
1               5                   10                  15

Ser Phe Asn Gly Arg Lys Leu Arg Pro Leu Val Pro Arg Pro Ile Pro
                20                  25                  30

Ser Thr Asn Asn Thr Pro Thr Ala Ser Ser Pro Pro Cys Leu Gly Ser
            35                  40                  45

Arg Leu His Asn Thr Asp Phe Phe Ala Leu Asn Gln Tyr His Leu Ala
        50                  55                  60

Ser Met Ala Asp Gln Asn Lys Arg Glu Phe Asn Thr Gln Pro Val Val
65                  70                  75                  80

Met Ser Ser Arg Trp Asn Pro Thr Pro Glu Gln Leu Arg Thr Leu Glu
                85                  90                  95

Asp Leu Tyr Arg Arg Gly Thr Arg Thr Pro Ser Thr Asp Gln Ile Gln
                100                 105                 110

Asp Ile Thr Ala Gln Leu Arg Arg Tyr Gly Arg Ile Glu Gly Lys Asn
            115                 120                 125

Val Phe Tyr Trp Phe Gln Asn His Lys Ala Arg Glu Arg Gln Lys Arg
        130                 135                 140

Arg Arg Gln Met Glu Ser Asp Ser Phe Asp Gly His Leu Gln Asn Gly
```

His Gly Ile Glu Ile Phe Glu Arg Lys Glu Ser Glu Ala Ser Arg Thr
145                 150                 155                 160

Gly Tyr Glu Gly Glu Gln Thr Lys Asn Trp Ala Pro Ser Thr Asn Cys
            165                 170                 175

Ser Thr Leu Ser Glu Glu Ser Val Ser Ile Ser Arg Ala Thr Lys Gly
                180                 185                 190

Ala Met Ala Glu Tyr Cys Arg Pro Asp Gly Trp Met Gln Leu Asp Glu
    195                 200                 205

Gly Glu Leu Gln His Arg Arg Asn Phe Ile Glu Arg Asn Ala Thr Trp
210                 215                 220

Glu Met Met Gln Leu Ser Cys Pro Ser Pro Thr His Gln Arg Asn Thr
225                 230                 235                 240

Ile Ser Ser Thr Ser Ser Thr Thr Met Ser Lys Gln Gly Ala Ala
                245                 250                 255

Ala Ala Lys Leu Ile Lys Ala His Asp Leu Asn Val Phe Ile Ala Pro
    260                 265                 270

Tyr Arg Glu Asn Gly His His Gly Ala Leu Ile Asn Gln Phe Asn Ser
275                 280                 285

Ser Val Ile Asn Asp Gly Asp Glu Ser Arg Gly Gly Thr Gly Glu Ser
290                 295                 300

Gln Thr Leu Gln Leu Phe Pro Leu Arg Ser Gly Gly Asp Gly Asn Asn
305                 310                 315                 320

Asn Ile Glu Ser Ile Asn Glu Arg Glu Ser Glu Val Ser Val Ser Ala
    325                 330                 335

Ala Glu Ala Leu Asn Ala Asn Asn Phe Ala Pro Cys Gln Phe Phe Glu
340                 345                 350

Phe Leu Pro Leu Lys His
    355                 360

365

370

<210> SEQ ID NO 13
<211> LENGTH: 1188
<212> TYPE: DNA
<213> ORGANISM: Nicotiana benthamiana

<400> SEQUENCE: 13
atgtggatgg tgggttacaa tgacggggga gatttcaaca tgcaggattc attcaatgga      60
agaaagcttc gtccactaat gccaagagta cctcatcttc ccactgctaa tatttctact     120
aatccaactt gtttaagaag tattcatggc gaaaatttta ttgcacttaa tcaccatcag     180
cttgctatga gtgagcaaaa taagagagat tttaatacac agcaattagt tgtgagctca     240
cgttggaatc caactccaga caacttcaa accctagagg agttgtatcg acgtggcacg      300
agaactcctt cagctgaaca gattcagcat attactgctc aacttcgacg ctatgggaaa     360
attgaaggca agaatgtttt ttactggttt caaaatcaca aggctaggga acgccaaaaa     420
cgacgccgtc aacttgaatc agctggtgct gctgctgcta atgctggtgg agatgatcag     480
tctcgtaata attgtaaccc tgaaaacacc gaaaggaaag aatcaggggc aaataggaca     540
ggatttgaaa ttgaacagac caagaactgg ccatctccaa caaactgcag tactcttgca     600
gagaaaactg tggcaacaac aaaggcagca gcagcaggag tggcagaatg tagagtagca     660
gcagaaagat ggataccatt cgatgaagga gaacaaagaa ggagcctatt actagctgat     720
caaaggaatg ccacgtggca gatgatgcat tgtcttgtt cacctcctac caccaccacc     780
ccgcatcatc atctcatgaa caacagcatt tctactgcat caattagtaa tactatcact     840

```
gctactacta ctccaataat atgcagtagt actactccat caacactaag aacaacaatg      900
gagccaaagc aactcttcaa aaccaaagat catctcaata ttattatagc acccttttaga     960 acagataatc ataaacacga aaacatggaa aacattttttg gagacgaagg acaggaagaa   1020
tctcagaccc ttgaattgtt tcctctccgc agcagcaatg caacaacga cgataataat    1080 tttcaggaga aggatgaagt agagatatca ggggccgatg ataattcgaa cagtaacttt    1140
agtggtagtc attgccagtt ttttgagttt cttcccttga aaaactga                 1188
```

<210> SEQ ID NO 14
<211> LENGTH: 395
<212> TYPE: PRT
<213> ORGANISM: Nicotiana benthamiana

<400> SEQUENCE: 14

```
Met Trp Met Val Gly Tyr Asn Asp Gly Gly Asp Phe Asn Met Gln Asp
  1               5                  10                  15

Ser Phe Asn Gly Arg Lys Leu Arg Pro Leu Met Pro Arg Val Pro His
             20                  25                  30

Leu Pro Thr Ala Asn Ile Ser Thr Asn Pro Thr Cys Leu Arg Ser Ile
         35                  40                  45

His Gly Glu Asn Phe Ile Ala Leu Asn His His Gln Leu Ala Met Ser
     50                  55                  60

Glu Gln Asn Lys Arg Asp Phe Asn Thr Gln Gln Leu Val Val Ser Ser
 65                  70                  75                  80

Arg Trp Asn Pro Thr Pro Glu Gln Leu Gln Thr Leu Glu Glu Leu Tyr
                 85                  90                  95

Arg Arg Gly Thr Arg Thr Pro Ser Ala Glu Gln Ile Gln His Ile Thr
            100                 105                 110

Ala Gln Leu Arg Arg Tyr Gly Lys Ile Glu Gly Lys Asn Val Phe Tyr
        115                 120                 125

Trp Phe Gln Asn His Lys Ala Arg Glu Arg Gln Lys Arg Arg Arg Gln
    130                 135                 140

Leu Glu Ser Ala Gly Ala Ala Ala Asn Ala Gly Gly Asp Asp Gln
145                 150                 155                 160

Ser Arg Asn Asn Cys Asn Pro Glu Asn Thr Glu Arg Lys Glu Ser Gly
                165                 170                 175

Ala Asn Arg Thr Gly Phe Glu Ile Glu Gln Thr Lys Asn Trp Pro Ser
            180                 185                 190

Pro Thr Asn Cys Ser Thr Leu Ala Glu Lys Thr Val Ala Thr Thr Lys
        195                 200                 205

Ala Ala Ala Ala Gly Val Ala Glu Cys Arg Val Ala Ala Glu Arg Trp
    210                 215                 220

Ile Pro Phe Asp Glu Gly Glu Gln Arg Arg Ser Leu Leu Leu Ala Asp
225                 230                 235                 240

Gln Arg Asn Ala Thr Trp Gln Met Met His Leu Ser Cys Ser Pro Pro
                245                 250                 255

Thr Thr Thr Thr Pro His His His Leu Met Asn Asn Ser Ile Ser Thr
            260                 265                 270

Ala Ser Ile Ser Asn Thr Ile Thr Ala Thr Thr Pro Ile Ile Cys
        275                 280                 285

Ser Ser Thr Thr Pro Ser Thr Leu Arg Thr Thr Met Glu Pro Lys Gln
    290                 295                 300

Leu Phe Lys Thr Lys Asp His Leu Asn Ile Ile Ile Ala Pro Phe Arg
```

```
                305                 310                 315                 320
Thr Asp Asn His Lys His Glu Asn Met Glu Asn Ile Phe Gly Asp Glu
                    325                 330                 335

Gly Gln Glu Glu Ser Gln Thr Leu Glu Leu Phe Pro Leu Arg Ser Ser
                    340                 345                 350

Asn Asp Asn Asn Asp Asn Asn Phe Gln Glu Lys Asp Glu Val Glu
                    355                 360                 365

Ile Ser Gly Ala Asp Asp Asn Ser Asn Ser Asn Phe Ser Gly Ser His
                370                 375                 380

Cys Gln Phe Phe Glu Phe Leu Pro Leu Lys Asn
385                 390                 395
```

<210> SEQ ID NO 15
<211> LENGTH: 951
<212> TYPE: DNA
<213> ORGANISM: Glycine max

<400> SEQUENCE: 15

```
atgtggatgg ttggttacaa tgaaggagct gagttcaaca tggccgatta tggattcaat      60
ggaaggaaac taaggcctct catgccaagg ccagtcactt ctcctaacaa tacttcaaac     120
actaactctc catacttgac ccgcattcat catggcaacg atttcttttc acagtatcac     180
aatcttgcat cagtggcaga tcagggaaag agagagttca accctccacc agtagtggtg     240
agttcaaggt ggaatccaac cccggagcaa ctgagagcat ggaggaatt gtatagaaga      300
gggacaagaa caccatctgc ggagcaaatc aacaaatca cggcacagct taggaggttt      360
ggaaaaattg aagggaagaa tgtcttctat tggtttcaga atcacaaagc aagagaaaga     420
cagaaacgcc gccgtcaaat ggagtcagtt gtagctgagg tcatcacac ccgtgacttt      480
gatagtactc ttgaaaagaa gacttcggaa tctgttacaa tacaaagggc agcaaaagca     540
gccattgcag agtgtagaac agatggatgg ctccaattcg atgaaggaga gttacaacat     600
agaagaaact ttatggagag aatgccacg tggcatatga tgcagttacc ttgtcctccc      660
cctcctacag tttcacccca cctcataaac acaccatctc ctactactag catggccccc     720
gcaaccacag taacagcaag actaatggac ccaaagctca ttaagactca tgatctcagc     780
ttctttattt cacctaacac taacagagaa acggtatta tccacttaag cagtatcagc      840
acccaggatc ataataattc tgtggaatct caaacccttc aacttttttcc aataaggaac    900
aacgcggatg aaagcagctg tgataacatc aaccaccaaa aagagacaga g              951
```

<210> SEQ ID NO 16
<211> LENGTH: 317
<212> TYPE: PRT
<213> ORGANISM: Glycine max

<400> SEQUENCE: 16

```
Met Trp Met Val Gly Tyr Asn Glu Gly Ala Glu Phe Asn Met Ala Asp
1               5                   10                  15

Tyr Gly Phe Asn Gly Arg Lys Leu Arg Pro Leu Met Pro Arg Pro Val
                20                  25                  30

Thr Ser Pro Asn Asn Thr Ser Asn Thr Asn Ser Pro Tyr Leu Thr Arg
                35                  40                  45

Ile His His Gly Asn Asp Phe Phe Ser Gln Tyr His Asn Leu Ala Ser
            50                  55                  60

Val Ala Asp Gln Gly Lys Arg Glu Phe Asn Pro Pro Val Val Val
65              70                  75                  80
```

```
Ser Ser Arg Trp Asn Pro Thr Pro Glu Gln Leu Arg Ala Leu Glu Glu
            85                  90                  95

Leu Tyr Arg Arg Gly Thr Arg Thr Pro Ser Ala Glu Gln Ile Gln Gln
            100                 105                 110

Ile Thr Ala Gln Leu Arg Arg Phe Gly Lys Ile Glu Gly Lys Asn Val
            115                 120                 125

Phe Tyr Trp Phe Gln Asn His Lys Ala Arg Glu Arg Gln Lys Arg Arg
        130                 135                 140

Arg Gln Met Glu Ser Val Val Ala Glu Gly His His Thr Arg Asp Phe
145                 150                 155                 160

Asp Ser Thr Leu Glu Lys Lys Thr Ser Glu Ser Val Thr Ile Gln Arg
                165                 170                 175

Ala Ala Lys Ala Ala Ile Ala Glu Cys Arg Thr Asp Gly Trp Leu Gln
            180                 185                 190

Phe Asp Glu Gly Glu Leu Gln His Arg Arg Asn Phe Met Glu Arg Asn
        195                 200                 205

Ala Thr Trp His Met Met Gln Leu Pro Cys Pro Pro Pro Thr Val
210                 215                 220

Ser Pro His Leu Ile Asn Thr Pro Ser Pro Thr Thr Ser Met Ala Pro
225                 230                 235                 240

Ala Thr Thr Val Thr Ala Arg Leu Met Asp Pro Lys Leu Ile Lys Thr
            245                 250                 255

His Asp Leu Ser Phe Phe Ile Ser Pro Asn Thr Asn Arg Glu Asn Gly
            260                 265                 270

Ile Ile His Leu Ser Ser Ile Ser Thr Gln Asp His Asn Asn Ser Val
        275                 280                 285

Glu Ser Gln Thr Leu Gln Leu Phe Pro Ile Arg Asn Asn Ala Asp Glu
    290                 295                 300

Ser Ser Cys Asp Asn Ile Asn His Gln Lys Glu Thr Glu
305                 310                 315

<210> SEQ ID NO 17
<211> LENGTH: 1113
<212> TYPE: DNA
<213> ORGANISM: Medicago sativa

<400> SEQUENCE: 17
atggctgatt atccattcag tggaaggaaa ctaaggcctc tcattccaag accagtccca      60
gtccctacta cttctcctaa caacacttca actataaccc cttccttaaa ccgcattcat     120
ggtggcaatg atttattttc acaatatcat cataatctgc agcagcaagc atcagtagga     180
gatcatagca agagatcaga gttgaataat aataataatc catctgcagc agttgtggtg     240
agttcaagat ggaatccaac accagaacag ttaagagcac tggaagaatt gtatagaaga     300
ggaacaagaa caccttctgc tgagcaaatc caacaaataa ctgcccagct tagagaattt     360
ggaaaaattg aaggcaaaaa tgttttctat tggtttcaga atcacaaagc cagagaaagg     420
caaaaacgac ggcgtcaaat ggaatcagca gctgctgagt ttgattctgc tattgaaaag     480
aaagacttag cgcaagtag acagtgtttt gaagttgaac acactaaaaa ctggctacca     540
tctacaaatt ccagtaccag tactcttcct cttgcagagg aatctgtttc aattcaaagg     600
gcagcagcag cagcagcaaa agcagatcag tactctagaa cagatggatg gctccaattc     660
gatgaagcag aattacagca agaagaaaac tttatggaaa ggaatgccac gtggcatatg     720
atgcagttaa cttcttcttg tcctacccct ctaaacacct ctactacaac aacagctagc     780
```

```
gtggccacca caaccacagt aacaactaga cttatggacc caaaactcat caagacccat    840
gatttcaact tattcatttc acctcacaca tactacaact acaaagaaag ggaaaacgct    900
tttatccact taaacagtat caactacaat agtactcatc aaaatgaatc tgatcaaacc    960
cttcaacttt tcccaataag gaatggagat catggatgca ctaatgatga tcatcatcat   1020
aacatcatta accaacacaa agagacagag atatcagctt cagcaatcaa tgcacccaac   1080
cagtttattg agtttcttcc cttgaaaaac tga                                1113
```

<210> SEQ ID NO 18
<211> LENGTH: 370
<212> TYPE: PRT
<213> ORGANISM: Medicago sativa

<400> SEQUENCE: 18

```
Met Ala Asp Tyr Pro Phe Ser Gly Arg Lys Leu Arg Pro Leu Ile Pro
1               5                   10                  15

Arg Pro Val Pro Val Pro Thr Thr Ser Pro Asn Asn Thr Ser Thr Ile
            20                  25                  30

Thr Pro Ser Leu Asn Arg Ile His Gly Gly Asn Asp Leu Phe Ser Gln
        35                  40                  45

Tyr His His Asn Leu Gln Gln Gln Ala Ser Val Gly Asp His Ser Lys
    50                  55                  60

Arg Ser Glu Leu Asn Asn Asn Asn Pro Ser Ala Ala Val Val Val
65                  70                  75                  80

Ser Ser Arg Trp Asn Pro Thr Pro Glu Gln Leu Arg Ala Leu Glu Glu
                85                  90                  95

Leu Tyr Arg Arg Gly Thr Arg Thr Pro Ser Ala Glu Gln Ile Gln Gln
            100                 105                 110

Ile Thr Ala Gln Leu Arg Glu Phe Gly Lys Ile Glu Gly Lys Asn Val
        115                 120                 125

Phe Tyr Trp Phe Gln Asn His Lys Ala Arg Glu Arg Gln Lys Arg Arg
    130                 135                 140

Arg Gln Met Glu Ser Ala Ala Ala Glu Phe Asp Ser Ala Ile Glu Lys
145                 150                 155                 160

Lys Asp Leu Gly Ala Ser Arg Thr Val Phe Glu Val Glu His Thr Lys
                165                 170                 175

Asn Trp Leu Pro Ser Thr Asn Ser Ser Thr Ser Thr Leu Pro Leu Ala
            180                 185                 190

Glu Glu Ser Val Ser Ile Gln Arg Ala Ala Ala Ala Ala Lys Ala
        195                 200                 205

Asp Gln Tyr Ser Arg Thr Asp Gly Trp Leu Gln Phe Asp Glu Ala Glu
    210                 215                 220

Leu Gln Gln Arg Arg Asn Phe Met Glu Arg Asn Ala Thr Trp His Met
225                 230                 235                 240

Met Gln Leu Thr Ser Ser Cys Pro Thr Leu Leu Asn Thr Ser Thr Thr
                245                 250                 255

Thr Thr Ala Ser Val Ala Thr Thr Thr Val Thr Thr Arg Leu Met
            260                 265                 270

Asp Pro Lys Leu Ile Lys Thr His Asp Phe Asn Leu Phe Ile Ser Pro
        275                 280                 285

His Thr Tyr Tyr Asn Tyr Lys Glu Arg Glu Asn Ala Phe Ile His Leu
    290                 295                 300

Asn Ser Ile Asn Tyr Asn Ser Thr His Gln Asn Glu Ser Asp Gln Thr
```

```
                305                 310                 315                 320
Leu Gln Leu Phe Pro Ile Arg Asn Gly Asp His Gly Cys Thr Asn Asp
                    325                 330                 335

Asp His His His Asn Ile Ile Asn Gln His Lys Glu Thr Glu Ile Ser
                340                 345                 350

Ala Ser Ala Ile Asn Ala Pro Asn Gln Phe Ile Glu Phe Leu Pro Leu
            355                 360                 365

Lys Asn
    370

<210> SEQ ID NO 19
<211> LENGTH: 1200
<212> TYPE: DNA
<213> ORGANISM: Nicotiana sylvestris

<400> SEQUENCE: 19
atgtggatga tgggttacaa cgacggggga gatttcaaca tgcaggattc attcaatgga      60
agaaagcttc gtccactaat gccaagagta cctcatcttc ccactgctaa tatttctact     120
aatccaactt gtttaagaag tattcatggc gaaaattttg ttgcacttaa tcaccatcag     180
cttgctatga gtgagcaaaa taagagagat tttaatacac aacaattagt tgtgagctca     240
cgttggaatc caactccaga acaacttcaa accctagagg agttgtatcg acgtggcacg     300 agaaccctt cagctgaaca gattcagcat attactgctc aacttcgacg ctatgggaaa      360
attgaaggca agaatgtttt ttactggttt caaaatcaca aggctaggga cgccaaaaa      420 cgacgccgtc aacttgaatc cgctgctggt ggaggtgctg caaatgctgc tggtggtgga     480
gatgatcagt ctcgtagtaa ttgtaaccct gaaaacaccg aaaggaaaga atcaggggca     540
aataggacag gatttgaaat tgaacagacc aagaactggc catccccaac aaactgcagt     600
actcttgcag agaaaactgt ggcaacaaca aaagcagcag cagcaggagg agtggcagaa     660
tgtagagtag cagcagaaag atggatacca ttcgatgaag agaacaaag aaggagccta     720 ttactagctg atcaaaggaa tgccacgtgg cagatgatgc atttgtcttg ttcaccaccc     780
acctccacca cccccccatca tcatctcatg aacatcaact catctactgc agcaattagt     840
aatactatat ctggaactac ttctccaata atatgcagta gtaatactcc atcaacacca     900
agaacgacaa tggagccaaa gcaactcttc aaaaccaaag atcatctcaa tatatttata     960 gcaccctta gaacagataa tcgtaaacac gaaaatatgg aaaacattgt tggagacgaa     1020
ggacaggaag aatctcagac ccttgaattg tttcctctcc gcagcagcaa tgataacaac     1080
gacgataata attttcgga gaaggatgaa gtagagatat caggggccga tgctaactcg     1140
aacagtaact ttagtggtag tcattaccag ttttttgagt ttcttccact taaaaactaa     1200

<210> SEQ ID NO 20
<211> LENGTH: 399
<212> TYPE: PRT
<213> ORGANISM: Nicotania sylvestris

<400> SEQUENCE: 20

Met Trp Met Met Gly Tyr Asn Asp Gly Gly Asp Phe Asn Met Gln Asp
1               5                   10                  15

Ser Phe Asn Gly Arg Lys Leu Arg Pro Leu Met Pro Arg Val Pro His
                20                  25                  30

Leu Pro Thr Ala Asn Ile Ser Thr Asn Pro Thr Cys Leu Arg Ser Ile
            35                  40                  45
```

```
His Gly Glu Asn Phe Val Ala Leu Asn His His Gln Leu Ala Met Ser
    50                  55                  60

Glu Gln Asn Lys Arg Asp Phe Asn Thr Gln Gln Leu Val Val Ser Ser
65                  70                  75                  80

Arg Trp Asn Pro Thr Pro Glu Gln Leu Gln Thr Leu Glu Glu Leu Tyr
                85                  90                  95

Arg Arg Gly Thr Arg Thr Pro Ser Ala Glu Gln Ile Gln His Ile Thr
            100                 105                 110

Ala Gln Leu Arg Arg Tyr Gly Lys Ile Glu Gly Lys Asn Val Phe Tyr
        115                 120                 125

Trp Phe Gln Asn His Lys Ala Arg Glu Arg Gln Lys Arg Arg Arg Gln
    130                 135                 140

Leu Glu Ser Ala Ala Gly Gly Ala Ala Asn Ala Ala Gly Gly Gly
145                 150                 155                 160

Asp Asp Gln Ser Arg Ser Asn Cys Asn Pro Glu Asn Thr Glu Arg Lys
                165                 170                 175

Glu Ser Gly Ala Asn Arg Thr Gly Phe Glu Ile Glu Gln Thr Lys Asn
            180                 185                 190

Trp Pro Ser Pro Thr Asn Cys Ser Thr Leu Ala Glu Lys Thr Val Ala
        195                 200                 205

Thr Thr Lys Ala Ala Ala Gly Gly Val Ala Glu Cys Arg Val Ala
    210                 215                 220

Ala Glu Arg Trp Ile Pro Phe Asp Glu Gly Glu Gln Arg Arg Ser Leu
225                 230                 235                 240

Leu Leu Ala Asp Gln Arg Asn Ala Thr Trp Gln Met Met His Leu Ser
                245                 250                 255

Cys Ser Pro Pro Thr Ser Thr Thr Pro His His His Leu Met Asn Ile
            260                 265                 270

Asn Ser Ser Thr Ala Ala Ile Ser Asn Thr Ile Ser Gly Thr Thr Ser
        275                 280                 285

Pro Ile Ile Cys Ser Ser Asn Thr Pro Ser Thr Pro Arg Thr Thr Met
    290                 295                 300

Glu Pro Lys Gln Leu Phe Lys Thr Lys Asp His Leu Asn Ile Phe Ile
305                 310                 315                 320

Ala Pro Phe Arg Thr Asp Asn Arg Lys His Glu Asn Met Glu Asn Ile
                325                 330                 335

Val Gly Asp Glu Gly Gln Glu Glu Ser Gln Thr Leu Glu Leu Phe Pro
            340                 345                 350

Leu Arg Ser Ser Asn Asp Asn Asn Asp Asp Asn Asn Phe Ser Glu Lys
        355                 360                 365

Asp Glu Val Glu Ile Ser Gly Ala Asp Ala Asn Ser Asn Ser Asn Phe
    370                 375                 380

Ser Gly Ser His Tyr Gln Phe Phe Glu Phe Leu Pro Leu Lys Asn
385                 390                 395

<210> SEQ ID NO 21
<211> LENGTH: 1224
<212> TYPE: DNA
<213> ORGANISM: Populus trichocarpa

<400> SEQUENCE: 21
atgtggatga tgggttacaa tgatagtggt gacttcgaca tgccagattc tttcaatgac      60
aggaagctta agactctagt tccgaggcca ctaccctcca caaacaacac ttcaactgcc     120
tctggccatc cttgccctgg cagccgtctt catagtaccg attttcttgc tctaaatcag     180
```

```
taccatctgg gactggcaag tatggttgat caaggcataa gagagttcaa cacacagcca    240
gttgtaatga gctcaagatg gaatccaaca ccagaacagt taaggaccct cgaggagttg    300
tatcgaagag ggactagaac accctcaact gaccagattc aagacataac tgcacagctt    360
cgtagatatg gaagaattga aggaaagaat gtgttctact ggtttcaaaa ccacaaggcg    420
agagaaggc aaaaacgtcg acgtcaaatg gaatctgatt ctcttgatga tcatcagcaa    480
aatggacatg gtgttgaaat gtttgaaagg aagaaccag agaagtttga gatcatctat    540
gtattgcttc atagcattcc aattgttggt tttagagaga gatcaagtat gacaggttat    600
gaaggtgaac agaccaggaa ctgggctccc tctacaaaact gcagtacact atcagaggaa    660
tctgtttcaa tatcaaaggc aacaaaagca gcaatggcag agtactatag accagatgga    720
tggatcgaat cgatgaagg agaaataatg cagcatagaa ggaacctcat agaaaggaat    780
gcgacgtggg agatgatgcc gttttcttgc ccatctccca cccacctatt aaacactata    840
tctagcgcta ctgctacaac tatagctact acaagtgcgt caacacaagg agcggcaaca    900
gtaagaacaa tggacccaac aaagctcatg aacgctcatg acctcaacat ctttatagca    960
ccttacatag aaaatggtta tcatggagcc cgtattaacc acttcaataa cagcgtcatc   1020
aacgagggag gtgaatattg cagagatggc aatgacgaat ctcaaaccct tcaactattt   1080
cctattcgta gtggcggtaa cggaaacaat attgaaagaa ttaacgagag agagactgag   1140
gtatcggttt ctgctactga aaccttgaat gctaacgact tctctccttg ccagtttttc   1200
gagttccttc cactgaggat ctaa                                         1224
```

<210> SEQ ID NO 22
<211> LENGTH: 407
<212> TYPE: PRT
<213> ORGANISM: Populus trichocarpa

<400> SEQUENCE: 22

Met Trp Met Met Gly Tyr Asn Asp Ser Gly Asp Phe Asp Met Pro Asp
1               5                   10                  15

Ser Phe Asn Asp Arg Lys Leu Lys Thr Leu Val Pro Arg Pro Leu Pro
                20                  25                  30

Ser Thr Asn Asn Thr Ser Thr Ala Ser Gly His Pro Cys Pro Gly Ser
        35                  40                  45

Arg Leu His Ser Thr Asp Phe Leu Ala Leu Asn Gln Tyr His Leu Gly
    50                  55                  60

Leu Ala Ser Met Val Asp Gln Gly Ile Arg Glu Phe Asn Thr Gln Pro
65                  70                  75                  80

Val Val Met Ser Ser Arg Trp Asn Pro Thr Pro Glu Gln Leu Arg Thr
                85                  90                  95

Leu Glu Glu Leu Tyr Arg Arg Gly Thr Arg Thr Pro Ser Thr Asp Gln
                100                 105                 110

Ile Gln Asp Ile Thr Ala Gln Leu Arg Arg Tyr Gly Arg Ile Glu Gly
            115                 120                 125

Lys Asn Val Phe Tyr Trp Phe Gln Asn His Lys Ala Arg Glu Arg Gln
        130                 135                 140

Lys Arg Arg Arg Gln Met Glu Ser Asp Ser Leu Asp Asp His Gln Gln
145                 150                 155                 160

Asn Gly His Gly Val Glu Met Phe Glu Arg Lys Glu Pro Glu Lys Phe
                165                 170                 175

Glu Ile Ile Tyr Val Leu Leu His Ser Ile Pro Ile Val Gly Phe Arg

```
           180              185              190
Glu Arg Ser Ser Met Thr Gly Tyr Glu Gly Glu Gln Thr Arg Asn Trp
                195              200              205

Ala Pro Ser Thr Asn Cys Ser Thr Leu Ser Glu Ser Val Ser Ile
    210              215              220

Ser Lys Ala Thr Lys Ala Ala Met Ala Glu Tyr Tyr Arg Pro Asp Gly
225              230              235              240

Trp Ile Glu Phe Asp Glu Gly Glu Ile Met Gln His Arg Arg Asn Leu
                245              250              255

Ile Glu Arg Asn Ala Thr Trp Glu Met Met Pro Phe Ser Cys Pro Ser
            260              265              270

Pro Thr His Leu Leu Asn Thr Ile Ser Ser Ala Thr Ala Thr Thr Ile
        275              280              285

Ala Thr Thr Ser Ala Ser Thr Gln Gly Ala Ala Thr Val Arg Thr Met
            290              295              300

Asp Pro Thr Lys Leu Met Asn Ala His Asp Leu Asn Ile Phe Ile Ala
305              310              315              320

Pro Tyr Ile Glu Asn Gly Tyr His Gly Ala Arg Ile Asn His Phe Asn
                325              330              335

Asn Ser Val Ile Asn Glu Gly Gly Glu Tyr Cys Arg Asp Gly Asn Asp
            340              345              350

Glu Ser Gln Thr Leu Gln Leu Phe Pro Ile Arg Ser Gly Gly Asn Gly
        355              360              365

Asn Asn Ile Glu Arg Ile Asn Glu Arg Glu Thr Glu Val Ser Val Ser
    370              375              380

Ala Thr Glu Thr Leu Asn Ala Asn Asp Phe Ser Pro Cys Gln Phe Phe
385              390              395              400

Glu Phe Leu Pro Leu Arg Ile
                405

<210> SEQ ID NO 23
<211> LENGTH: 1206
<212> TYPE: DNA
<213> ORGANISM: Ricinus communis

<400> SEQUENCE: 23
atgtggatga tgggttatag tgatggtggt gagttcaaca tgacagcaga ttccttcaat      60
ggcaggaagc ttaggcctct cattccaagg acaccagggc taattctac aaacaacact     120 tctaactcta gccctcctac acttagccgt cttcatggca ctgatttctt ttcactaaat     180
caccatctgg caactatggc tgatcaaagc aaaagagatt ccatacaca accagttgta     240 gtgagttcaa gatggaaccc aacaccagag cagttaaggg cacttgaaga attgtataga     300
agagggacta ggactccaac aacagaacag attgaacaca taacaaagca actcagaaga     360
tatggaaaga ttgaagggaa gaacgtattc tactggttcc aaaaccacaa ggcaagagaa     420
aggcaaaaac gtcgccgtca atggaatctg cagtccctg atcacgacca gcagcagcag     480
caacaacatc atgacataga aatctttgaa agtaaagaat cagaagcaaa taggacaggt     540
tatgaaggtg aacagaccaa gaactggcct ccctctacta actgcagtac actaccagag     600
gaatcaattt caatacatag agcagctaaa gcggcagtgg cagaatgtag agcaggcgat     660
ggattgatcc aattcgatga agtagaattt cagcatagaa ggagctttat ggagaggaat     720
gccacgtggc agatgatgca gttgtcttgt ccatctccca cccacctcat aaacactagc     780
tctagtacta gtactaacac tacttctaca actgctacaa ccctaacagc agcagcaaca     840
```

```
tcaacagcca caacaacaac atcgacagct ccaacagcag cagcaacaag aagaacaatg    900
gacccaaaac tcattaaaac ttcccatgac cttaatatct tcatagcccc ctattacaga    960
gaaaatggga atggccttat ttacaattat aacaacttca acaatagtca tgtcatcaac   1020
gaacaagata atgggtgtgg ggaatctcaa acacttcaac tctttcctct tcgtagtggt   1080
ggtggtggtg gtgatggtaa tgaaagcatt aatgataaag agactgagac atcagcagtt   1140
gctgcagcta tgaatgccaa cttcactcct taccagtttt ttgagttcct tccattgaaa   1200
aactaa                                                              1206
```

<210> SEQ ID NO 24
<211> LENGTH: 401
<212> TYPE: PRT
<213> ORGANISM: Ricinus communis

<400> SEQUENCE: 24

```
Met Trp Met Met Gly Tyr Ser Asp Gly Gly Glu Phe Asn Met Thr Ala
 1               5                  10                  15

Asp Ser Phe Asn Gly Arg Lys Leu Arg Pro Leu Ile Pro Arg Thr Pro
            20                  25                  30

Gly Pro Asn Ser Thr Asn Asn Thr Ser Asn Ser Ser Pro Thr Leu
        35                  40                  45

Ser Arg Leu His Gly Thr Asp Phe Phe Ser Leu Asn His His Leu Ala
    50                  55                  60

Thr Met Ala Asp Gln Ser Lys Arg Asp Phe His Thr Gln Pro Val Val
65                  70                  75                  80

Val Ser Ser Arg Trp Asn Pro Thr Pro Glu Gln Leu Arg Ala Leu Glu
                85                  90                  95

Glu Leu Tyr Arg Arg Gly Thr Arg Thr Pro Thr Thr Glu Gln Ile Glu
            100                 105                 110

His Ile Thr Lys Gln Leu Arg Arg Tyr Gly Lys Ile Glu Gly Lys Asn
        115                 120                 125

Val Phe Tyr Trp Phe Gln Asn His Lys Ala Arg Glu Arg Gln Lys Arg
    130                 135                 140

Arg Arg Gln Met Glu Ser Ala Val Pro Asp His Asp Gln Gln Gln Gln
145                 150                 155                 160

Gln Gln His His Asp Ile Glu Ile Phe Glu Ser Lys Glu Ser Glu Ala
                165                 170                 175

Asn Arg Thr Gly Tyr Glu Gly Glu Gln Thr Lys Asn Trp Pro Pro Ser
            180                 185                 190

Thr Asn Cys Ser Thr Leu Pro Glu Glu Ser Ile Ser Ile His Arg Ala
        195                 200                 205

Ala Lys Ala Ala Val Ala Glu Cys Arg Ala Gly Asp Gly Leu Ile Gln
    210                 215                 220

Phe Asp Glu Val Glu Phe Gln His Arg Arg Ser Phe Met Glu Arg Asn
225                 230                 235                 240

Ala Thr Trp Gln Met Met Gln Leu Ser Cys Pro Ser Pro Thr His Leu
                245                 250                 255

Ile Asn Thr Ser Ser Ser Thr Ser Thr Asn Thr Thr Ser Thr Thr Ala
            260                 265                 270

Thr Thr Leu Thr Ala Ala Ala Thr Ser Thr Ala Thr Thr Thr Thr Ser
        275                 280                 285

Thr Ala Pro Thr Ala Ala Ala Thr Arg Arg Thr Met Asp Pro Lys Leu
    290                 295                 300
```

Ile Lys Thr Ser His Asp Leu Asn Ile Phe Ile Ala Pro Tyr Tyr Arg
305                 310                 315                 320

Glu Asn Gly Asn Gly Leu Ile Tyr Asn Tyr Asn Asn Phe Asn Asn Ser
            325                 330                 335

His Val Ile Asn Glu Gln Asp Asn Gly Cys Gly Glu Ser Gln Thr Leu
        340                 345                 350

Gln Leu Phe Pro Leu Arg Ser Gly Gly Gly Gly Asp Gly Asn Glu
            355                 360                 365

Ser Ile Asn Asp Lys Glu Thr Glu Thr Ser Ala Val Ala Ala Ala Met
370                 375                 380

Asn Ala Asn Phe Thr Pro Tyr Gln Phe Phe Glu Phe Leu Pro Leu Lys
385                 390                 395                 400

Asn

<210> SEQ ID NO 25
<211> LENGTH: 1044
<212> TYPE: DNA
<213> ORGANISM: Vitis vinifera

<400> SEQUENCE: 25

```
atgtggatga tgggttacaa tgatggggga gagctgaata tgcctgattc attcaatggc    60
aggaagcttc ggcctctgat tccaagacca gctacttcta ccaacggcac tgcaactacc   120
acgtcttctt gtttaagccg catccatggg actgatcttt ttggactgaa tcaccatctg   180
gagcaaagca acattagaga gttcaataca actccagtca tagtgagctc acgttggaat   240
ccaaccccgg agcagctaag gaccctagaa gaattatatc ggcgcgggac tcgaacgcct   300
tcggctgagc aaattcagca tatcaccgca cagctccgcc gatacggcaa gattgaaggc   360
aagaatgtgt tttactggtt tcagaaccac aaggcaaggg aacggcagaa gcggcgccga   420
caacttgaac agatgagca gaatcgcgat gttgaaagca cagagaggaa ggaatcagga   480
ggaagtagga caggttttga gaacagacc aagaactggg cactctctac aaactgcagt   540
atacttgcag aggaatctct ttcaatacaa agggcagcaa agcaacagc tgcagcagca   600
gaatgtgaaa cagatggatg gatccaattc gatgaagggg aattacagca tagaagaagc   660
ttggtagaaa gaaatgccat ttggcagatg atgcagttgt cttgtccttc tcccaccacc   720
cacctcataa acacgactac tactacaaga accaaagaag ctgcagcagt tagaagaatg   780
gacccaaagc tcataaagac tcgagatctg aacatcttca tagctcccta cagatcagaa   840
ggtcataatc acttggccgg tgtcggcgcc gatcactcca acgaagaaga gggtggagaa   900
tcccaaaccc ttcagctgtt ccccctccgg agcggccatg gcaatgaaaa cattaatgaa   960
aaagagggcg agatatcggt tgctgccatg aataccaacc tcactcctca ccagtttttt  1020
gagttccttc cactgaagaa ttaa                                         1044
```

<210> SEQ ID NO 26
<211> LENGTH: 347
<212> TYPE: PRT
<213> ORGANISM: Vitis vinifera

<400> SEQUENCE: 26

Met Trp Met Met Gly Tyr Asn Asp Gly Gly Glu Leu Asn Met Pro Asp
1               5                   10                  15

Ser Phe Asn Gly Arg Lys Leu Arg Pro Leu Ile Pro Arg Pro Ala Thr
            20                  25                  30

```
Ser Thr Asn Gly Thr Ala Thr Thr Ser Ser Cys Leu Ser Arg Ile
        35                  40                  45

His Gly Thr Asp Leu Phe Gly Leu Asn His His Leu Glu Gln Ser Asn
 50                  55                  60

Ile Arg Glu Phe Asn Thr Thr Pro Val Ile Val Ser Ser Arg Trp Asn
 65                  70                  75                  80

Pro Thr Pro Glu Gln Leu Arg Thr Leu Glu Glu Leu Tyr Arg Arg Gly
                85                  90                  95

Thr Arg Thr Pro Ser Ala Glu Gln Ile Gln His Ile Thr Ala Gln Leu
            100                 105                 110

Arg Arg Tyr Gly Lys Ile Glu Gly Lys Asn Val Phe Tyr Trp Phe Gln
        115                 120                 125

Asn His Lys Ala Arg Glu Arg Gln Lys Arg Arg Gln Leu Glu Pro
130                 135                 140

Asp Glu Gln Asn Arg Asp Val Glu Ser Thr Glu Arg Lys Glu Ser Gly
145                 150                 155                 160

Gly Ser Arg Thr Gly Phe Glu Glu Gln Thr Lys Asn Trp Ala Leu Ser
                165                 170                 175

Thr Asn Cys Ser Ile Leu Ala Glu Glu Ser Leu Ser Ile Gln Arg Ala
            180                 185                 190

Ala Lys Ala Thr Ala Ala Ala Glu Cys Arg Thr Asp Gly Trp Ile
        195                 200                 205

Gln Phe Asp Glu Gly Glu Leu Gln His Arg Arg Ser Leu Val Glu Arg
    210                 215                 220

Asn Ala Ile Trp Gln Met Met Gln Leu Ser Cys Pro Ser Pro Thr Thr
225                 230                 235                 240

His Leu Ile Asn Thr Thr Thr Thr Arg Thr Lys Glu Ala Ala Ala
                245                 250                 255

Val Arg Arg Met Asp Pro Lys Leu Ile Lys Thr Arg Asp Leu Asn Ile
            260                 265                 270

Phe Ile Ala Pro Tyr Arg Ser Glu Gly His Asn His Leu Ala Gly Val
        275                 280                 285

Gly Ala Asp His Ser Asn Glu Glu Gly Gly Glu Ser Gln Thr Leu
    290                 295                 300

Gln Leu Phe Pro Leu Arg Ser Gly His Gly Asn Glu Asn Ile Asn Glu
305                 310                 315                 320

Lys Glu Gly Glu Ile Ser Val Ala Ala Met Asn Thr Asn Leu Thr Pro
                325                 330                 335

His Gln Phe Phe Glu Phe Leu Pro Leu Lys Asn
            340                 345
```

<210> SEQ ID NO 27
<211> LENGTH: 376
<212> TYPE: PRT
<213> ORGANISM: Unknown
<220> FEATURE:
<223> OTHER INFORMATION: PhMAW

<400> SEQUENCE: 27

```
Met Trp Met Met Gly Tyr Asn Asp Gly Gly Asp Phe Asn Met Pro Asp
 1               5                  10                  15

Ser Phe Asn Gly Arg Lys Leu Arg Pro Leu Met Pro Arg Ile Pro His
                20                  25                  30

Val Pro Thr Ala Thr Ser Ser Thr Asn Cys Leu Arg Ser Ile His Gly
            35                  40                  45
```

```
Asp Asn Phe Ile Ala Leu Asn His His Gln Leu Gly Met Ser Glu Pro
 50                  55                  60

Asn Lys Arg Asp Tyr Asn Thr Gln Gln Leu Val Val Ser Ser Arg Trp
 65                  70                  75                  80

Asn Pro Thr Pro Glu Gln Leu Gln Thr Leu Glu Glu Leu Tyr Arg Arg
                 85                  90                  95

Gly Thr Arg Thr Pro Ser Ala Glu Gln Ile Gln His Ile Thr Ala Gln
            100                 105                 110

Leu Arg Arg Tyr Gly Lys Ile Glu Gly Lys Asn Val Phe Tyr Trp Phe
        115                 120                 125

Gln Asn His Lys Ala Arg Glu Arg Gln Lys Arg Arg Gln Leu Glu
130                 135                 140

Ser Asn Ala Ala Asn Asp Gly Gly Gly Asp Glu Gln Ser Arg Asn
145                 150                 155                 160

Asn Cys Asn Val Glu Asn Ala Glu Arg Lys Asp Ser Gly Ala Gly Ala
                165                 170                 175

Asn Arg Thr Gly Phe Glu Ile Glu Gln Thr Lys Asn Trp Pro Ser Pro
            180                 185                 190

Thr Asn Cys Ser Thr Leu Ser Pro Glu Lys Thr Val Ala Thr Thr Lys
        195                 200                 205

Ala Ala Ala Val Ala Glu Tyr Arg Ser Ala Glu Arg Trp Ile Pro Phe
210                 215                 220

Asp Glu Gly Ala Thr Glu Met Gln Gln Arg Arg Ser Leu Leu Ala Glu
225                 230                 235                 240

Arg Asn Ala Thr Trp Gln Met Met His Leu Ser Cys Ser Pro Pro Thr
                245                 250                 255

Pro His His His Met Asn Asn Ser Ser Thr Ser Asn Thr Ile Thr Thr
            260                 265                 270

Thr Thr Thr Ile Ile Ser Ser Pro Ser Thr Pro Arg Thr Met Glu Pro
        275                 280                 285

Lys His Phe Pro Lys Val Lys Asp His Leu Asn Ile Phe Ile Thr Pro
290                 295                 300

Phe Arg Thr Asp Asp His Ser Lys His Ser Leu Ser Glu Ile His Gly
305                 310                 315                 320

Asp Ser Gln Thr Leu Glu Leu Phe Pro Leu Arg Ser Asn Asn Glu Ile
                325                 330                 335

Asn Asp Glu Asn Asn Ile Ser Glu Lys Asp Asp Ile Glu Ile Ser Gly
            340                 345                 350

Ala Val Ala Thr Ser Asn Thr Asn Phe Ser Gly Ser Asn Tyr Gln Phe
        355                 360                 365

Phe Glu Phe Leu Pro Leu Lys Asn
370                 375

<210> SEQ ID NO 28
<211> LENGTH: 5176
<212> TYPE: DNA
<213> ORGANISM: Medicago truncatula

<400> SEQUENCE: 28
tggcttggag tgtgattgct tccatcatgt tttgtcgttg caagatgcta gcagctgcag      60
ctcttgggaa atacagaaat tctcaatttt agactaagac cagtgtcacc tgatcgattt     120
tttatgaaaa caatgcaatt atgcgtgtac ctgtggacat actttgtata attggcttaa     180
cttttataaa cgaatctcaa ctctaatatt atcaaggaat caaaagctgt ttttcttaat     240
```

```
tcccccatg  cttttcttg  tttccaaata  ctattagtat  atatgcaaaa  aaagtagaca   300
tgttttgcct  ttcatcttc  tttcactgaa  acctgtatag  tatctaccct  tttcccaatg   360
catgtaccaa  atttaatcgt  tacctatttc  aattgatttt  taacactaca  cagctcacag   420
attgaaagag  tctctttatt  taataacttt  gttggcaaaa  aaataaaaa   taaaaactaa   480
ttagttttac  aaactctgct  gcagaactct  aggagaaagt  agatacatgt  aatcatcaaa   540
ttaaagattc  acgggcaaca  ttatgcaatg  tatagtata   gtatagtgta  cctaaaataa   600
agaaaagaaa  aaagaatgta  ttgggtacta  attggcttga  ttcatgaaat  agatgcatat   660
gttagttatg  aggtttgttt  ttattattgt  taaatgtac   taaaggacga  catgttggtg   720
gagaataaaa  cattcccatc  ctatctatct  atctatatac  ctccctccta  actcctaagt   780
ctaagttata  tatatatata  tatatatata  tatatactaa  acaccattga  ctaattgaag   840
ctgaagccta  aaaaggatga  aaagtttaaa  gtttatgggg  ccatatatat  atatatatat   900
atatatatat  cctagcaata  atatatttga  caactagtag  ctagcttagc  tagcaatgac   960
aatgagaaca  gaaatgacaa  tactgattag  ggcttttatg  gacagtgcag  tatgttatgt  1020
agtggggaga  tgagatatgc  acaatcaata  ttagagagag  ggggtcaca   gacacaatag  1080
acacattgct  ctgtgctgtg  gtttagtaat  ttgcatggta  ctttacttac  ttatctcatt  1140
acatattttg  cattgcatgc  actaataata  aataacagac  atacaaatag  tagggattca  1200
gaatttgcag  gtagtaggcc  ctctactcaa  caaaaagcta  gaataatta   atcaattata  1260
gctttcaaat  tccactacta  tatcagcggt  gacagagtct  cacacactag  ctcgagaatt  1320
gagtcattcc  atcataatga  ccaagggtt   ataccctaaga  ggcaaacaaa  gagagagaaa  1380
gaaagagagg  acatggacag  ttttgtttat  tactgaacta  ccctcctata  tatggccatg  1440
ttcaattta   ttcaataaat  gactctggac  catggaagca  agattccaaa  taagtaaca   1500
gtcattatat  tttttctaat  tttctatctt  cacttcaaaa  taaatttcac  atttctaatg  1560
cacagtcatt  tttttctttt  ccaaaccaca  ttttttatat  atttaatga   attgtctcta  1620
tcaattaagt  tatgttcacc  agaaatttat  catttaaatg  taacacaatc  aatttttct   1680
tgagcattta  tgattgaatt  tacgtgtaaa  tatcgattat  gaaatttcat  actaaaactc  1740
aagtaaaag   aacatatatt  agtggaagga  aaatatatac  ttgtatgatt  acaaccattt  1800
aaacatatat  catttgagca  gtcacaaaaa  tatattatt   ttaattattt  tctttgttca  1860
tataatactg  tatgtatgta  ttttattgag  aaagaagata  cttatatggt  attatcggat  1920
cgtagaggtg  aaaaaagaaa  gaagtattcg  agttgaaccg  tacatgcatg  gagattggac  1980
agcaaaatag  acaaagaaaa  gggtgaaaga  gggagcagtt  cggattgaga  attagtgtga  2040
aaggcacgag  acgtaaaaga  gaacaataaa  tgagtgatga  ggctcatgat  aaccctcatc  2100
atcgtcacgt  cgttttcat   tctctactcc  caataacaaa  tcaatctccc  agaattccac  2160
gcttctctct  ctccctctcc  ttaaagccta  gtcaacctca  tctctatctt  ttgtcccata  2220
ttcatccaac  aatattatac  cattctctct  ccctctcttg  caattcatgt  gacctagaag  2280
aagagttcat  tctattcagt  catcaatctc  cctcctcaac  taattaacaa  tggttatggt  2340
ttttgttatt  accatctcat  agcagcatca  atcaacctat  atatgccata  tatatgcacc  2400
cttttcattt  caactagcta  gctaggtctt  gccatttta   ttttggtcat  tgccactcac  2460
ttctttccc   tttttcta    acttcaactc  catttcaaat  taccataacc  acactcacta  2520
ccaaaatat   ttctatatct  aacaactact  cccactttc   catttcaatc  cccttcattt  2580
attatatgtg  ttttttaaca  cagtgtttat  agctagctaa  gtaacttcat  tccttctact  2640
```

```
atttataata attagccttt tagtgagaaa agccctagtt gacaacatgt ggatggtggg      2700
ttacaatgaa ggtggtgagt tcaacatggc tgattatcca ttcagtggaa ggaaactaag      2760
gcctctcatt ccaagaccag tcccagtccc tactacttct cctaacaaca cttcaactat      2820
aactccttcc ttaaaccgca ttcatggtgg caatgattta ttttcacaat atcatcacaa      2880
tctgcagcag caaggtatat actcttttct cttcttattt acaattacta tatgtatgta      2940
tgtttaaact aaaagtgtca tgatgatgtt ttatagcatc agtaggagat catagcaaga      3000
gatcagagtt gaataataat aataatccat ctgcagcagt tgtggtgagt tcaagatgga      3060
atccaacacc agaacagtta agagcactgg aagaattgta tagaagagga acaagaacac      3120
cttctgctga gcaaatccaa caaataactg cccagcttag aaaatttgga aaaattgaag      3180
gcaaaaatgt tttctattgg tttcagaatc acaaagccag agaaaggcaa aaacgacggc      3240
gtcaaatgga atcagcagct gctgagtttg attctgctat tgaaaagaaa gacttaggta      3300
attattaatt aataactgta attattttgt gttagaggaa tatccttatt acatacatag      3360
atgacatgct ttttctcatt cttgttggtt gagatgtaaa gttatattct ttttttgtttt     3420 tcttttttgtc aacaggcgca agtaggacag tgtttgaagt tgaacacact aaaaactggc     3480
taccatctac aaattccagt accagtactc ttcatcttgc agaggtctat tctctctcta      3540
atatttataa taatatctta ctttgctttc attcatcatc atgcatgtat gtactaaacc      3600
agacaaatac catctctttt tcctttacaa ctttgggttg ggacattcct cccttaatca      3660
atcaccaaaa agtctttaa ggaataataa tcataaggat ctttatccac ccactaagca      3720
ctgattatat gcatagagag agagattaga taactagtaa aaagtagtaa cttatatgca      3780
gcaatgcaca aagtaactag gtataggga aagtaagaaa ggaccatagt aggtaagaaa      3840
agaaaaggtt tcgttgtagt agtaatttgt tgggaaatga aaagggtcct aaaagctgca      3900
ttccttcctt tctgtcgggg ctgctgttat gaaacttagc tgggcttttg gggcttgtgc      3960
atattcattc aagtcaagtc agtagctttt gggcactccc ccattccatt attcttcttt      4020
ctatgaaatg aaatttagag accaccaaaa caagacaacc ctcaccttca cacctttgct      4080
ttaatttgac ttcacataga ccaacatcca cctttttttt ttttttttaat tttacttttt     4140 tgagtgcatg ctcatttgaa atccgtgcat gccctatgtt ttagttttttg tgttgaggtt     4200 aattaaattc tttctttgtt tctacaggaa tctgttcaa ttcaaaggtc agcagcagca      4260
aaagcagatg gatggctcca attcgatgaa gcagaattac agcaaagaag aaactttatg      4320
gaaaggaatg ccacgtggca tatgatgcag ttaacttctt cttgtcctac agctagcatg      4380
tccaccacaa ccacagtaac aactagactt atggacccaa aactcatcaa gacccatgaa      4440
ctcaacttat tcatttcacc tcacacatac aaagaaagag aaaacgcttt tatccactta      4500
aatactagta gtactcatca aaatgaatct gatcaaaccc ttcaacttttt cccaataagg     4560 aatggagatc atggatgcac tgatcatcat catcatcatc ataacattat caaagagaca     4620
cagatatcag cttcagcaat caatgcaccc aaccagttta ttgagtttct tcccttgaaa     4680
aactgattag aaaagacttt gcttttttgt ttgttaggtg ttggattttg ttggaaagtg     4740
gcactgttat tattgttatt gatgttatgt ttcaagaaat tggtgatgta ataggacact     4800
gaatttgaat caagtatttt ccttaaaatg catttggact atgttggttc aagtatttaa     4860 ataataaat tctaaagggt tggtgtttat aggccttatt taagtaactt gatgtttatg     4920
tatacacatg ttgctcctga tatatgaaga ataggaaagg aggaattaaa tgaagagttt     4980
```

-continued

```
ataaggaatt tgatgtgagg ggtttgattt tgatacatag tatctcaaat aggaataaga      5040
tgtgacagac ttagatgttg aagtaactat gaacatgggt gggagaattc ttttgttctt      5100
ttgctgcata cttgggaaaa aaaataaaat gctgtgtatt gcaatcaatg ttctggtgga      5160
gtaaactctg tagtcc                                                     5176

<210> SEQ ID NO 29
<211> LENGTH: 5670
<212> TYPE: DNA
<213> ORGANISM: Nicotania sylvestris

<400> SEQUENCE: 29
acaagtgggc tgtatagtaa ttagtagaga tggaattgag atacagacat acacgcacag        60
ggacacacct acaagagagc tatataggga gtatagacaa gattccgttt tgaggacagt       120
cattttcatt gcacctaaaa catgcatgtt aacctacccc ctgctttagt tacaccctat       180
tctggacgtg tattaagaat taagtaggcg ttttgatata aaaattataa ttttttaaaa       240
aatttagtat tcgaagttca attgaaaaat ggtatttgaa atttgaatta tatttggaca       300
tgcattttac tttaagaaaa atgttacagt tttgttagtg ggaaagaatt tgattttttg       360
ttgaaaaact cattttgaa ttttttttctt ttaaagaaac ttgaaaaatt tcatggacaa       420 acaattttt ttttgtatga acaaatgagt cctaagatct catgcaaaaa caccatttat        480
tcccccggag aagagaagaa ttcaggattt aaataatatt atggttttgg cgacttaatt       540
atgtgcgcaa tcactagtac caagacaaga agaggttgct ccgatggtca gcgattccct       600
tcgagtcacc aaaggagtaa tagctccaat aagaagatc aaagggaatc aaaaaagaaa        660
aaaaactcac gagtaccaaa atttcttgtt tgcgaatagt cttttattgt tttttttttt       720 ttttttttatc tttccaagta ttctcaatca aatttcatat atacgcgtgt tcagataaat       780
atgaataaat cacatgttta caagctcttc gtactgatgc acattgttat tttcttgtaa       840
catgatagac caacttcctt acacccaacc caagatgaga aatattgtac agtaatagca       900
aattgatagg actgaaacta tatttatata caccagatgc ggatctagga tttaaactct       960
atgggttcaa tctttaatgt ctttagcatt gaacccatag tatatttaaa gttatgggtt      1020
catatccact gagttcagtt gaacccggca ctcgattgtt gcatccgccc ctgtatacac      1080
cgtcctcatt ccagagattt ccttataact ttctaatata aagctctggt tatatacggt      1140
tcaactctca aggaagctaa ggattataat taaaataaac tcaatgtaaa atactcgaat      1200
gaattctacg aatttagaaa agaaaaaaaa aagtgatacg cgcccggtaa acaaagagaa      1260
aaaagaaaaa aggttatgaa ggaaaagaa agatatggat ataagaagag gtgtttaatt      1320
tttgattttt aagttatgaa gaaggtggta tataaaaagt agaggagtac tcaagagtgg      1380
gggtaatata ttaaaagttt acacacactt aatatttata tcaatccaat aaataaatat      1440
tactcccttc attcactttt acttgtcaac tatactaaaa atacattttc acttttactt      1500
gtccactata ctaaatcaag agaaagataa tatttttttt atgttttacc cctatcatta      1560
accattcatt cctcaaatca ttttccaaga cttttgaaaa tgtgatcatt attatgggta      1620
caattgtaaa atacatactt tatttatttt tccgaagaga atacaaagtt aaaagtgaac      1680
gattaaaagt aaacggatga agtaactgtc tcgatcatat atccgtagtc aattaatgca      1740
cactcatacc ttaatctata atttaaatat gatattattt ataattaa agtagatag         1800 cgaatgattt tgttatttat ttaccataat taaagaggga actatggaga tagaggggggc      1860 agttcggatt gagaataagt gtgaaaggga gaggacaagg aaagaacaat aaatgagcta      1920
```

| | |
|---|---|
| ggggtggtga tgaggcttat gataaccctc atgatcgtca cgtcgttttt ccttcacatt | 1980 |
| tatcgatatc tctcttctct cccagaattc cacgccttct tctttctttc tttttgtttc | 2040 |
| atttcattct ctcttcttaa ttccccttttt cctttccttc cttattccat tttgctttct | 2100 |
| ctcaccaggc cagtctttcc ttttctctct gtctaatttg tctcctctct cacgccttga | 2160 |
| gaattgagat atcagtgtag tcctacatac tactaagcta catgtcaaaa caattttatt | 2220 |
| tgtaaaattc aagcctagtc aacctcatgt tttgatcact ttgtttcaat ttaaaccaac | 2280 |
| accattctat cttctttctt tgtctctctc cttctctctt tctttctgtc tctattgttc | 2340 |
| catctctttc tcctgaatct tgccaaattc cttgtcttca gctccctctc cccacccttta | 2400 |
| aaagtcaccc attttagtta ttctccccct atttctttct ctcttttact tttaccatta | 2460 |
| caatatatac cttttcttac tttgaaactc gattgaccac ttatagttaa ttcttgtaac | 2520 |
| ttaaaagatc acctccattc tctttaaact tccttctttc tcttttcata aactcaaaaa | 2580 |
| catccaccgc ttgaactaat taagccccat ctcttaatta attagaagct aagccctagt | 2640 |
| tttaaaaaaa tgtggatgat gggttacaac gacggggag atttcaacat gcaggattca | 2700 |
| ttcaatggaa gaaagcttcg tccactaatg ccaagagtac ctcatcttcc cactgctaat | 2760 |
| atttctacta atccaacttg tttaagaagt attcatggcg aaaattttgt tgcacttaat | 2820 |
| caccatcagc ttggtaagta attaactgct agagattata tatactatat agagttgtct | 2880 |
| ttctactttt ctctttttac cctttccgtt cctttttttg catgcgtgac attgatactt | 2940 |
| tgtcttcctt cgtatataaa aaagtcata tatcaacaga tctaacgaat agccatatta | 3000 |
| tttaatttaa tggttgcaat ttttttttct ttttcacgca gctatgagtg agcaaaataa | 3060 |
| gagagatttt aatacacaac aattagttgt gagctcacgt tggaatccaa ctccagaaca | 3120 |
| acttcaaacc ctagaggagt tgtatcgacg tggcacgaga accccttcag ctgaacagat | 3180 |
| tcagcatatt actgctcaac ttcgacgcta tgggaaaatt gaaggcaaga atgtttttta | 3240 |
| ctggtttcaa aatcacaagg ctagggaacg ccaaaaacga cgccgtcaac ttgaatccgc | 3300 |
| tgctggtgga ggtgctgcaa atgctgctgg tggtggagat gatcagtctc gtagtaattg | 3360 |
| taaccctgaa aacaccgaaa ggaaagaatc aggtatacgt taatccatct gcttgtgtat | 3420 |
| agtttatgcc ggattaaagt cagaaattta tcaaaagatt tatagtaacc atttataaat | 3480 |
| atttgtattt agaagattca acaatttata tatatacaca taaaagaatt ttcagtacaa | 3540 |
| ttttccggca aaggaaatct aattgaagtg ttgaacccct tcaatgaaca tggctcctcc | 3600 |
| acatgatgag tttattgaac tcacaaatat ttatttaaac tctatatata aatatacatg | 3660 |
| tgaaaatctt gaaaattaga acaagtaata tgttataaat cttgaagggg gtggagcaca | 3720 |
| acatgcaact taacaaaaag acatgcaatg agaatgatac atgaaagaga gaaatttgtt | 3780 |
| tgatagcgtg tgatgataca ctaaatattc ttttattctt ttccaatcca tccacactcg | 3840 |
| tattttgttg ttatttaaaa tgtaaagttg cattcgtgtt tggattttga gagatatgct | 3900 |
| ttttcttctt ccattccgat tgttgcttga gatataaaaa ttttctttac tcttttgttt | 3960 |
| ttgtgttttgt cgtcgatatc gcaggggcaa ataggacagg atttgaaatt gaacagacca | 4020 |
| agaactggcc atccccaaca aactgcagta ctccttgcaga ggtccttccc tatatatttt | 4080 |
| ttcatttgcc tttttctttt ctctctcctt agactctgaa ttctcttttt cacaaccaaa | 4140 |
| ttaaaaagca attaaaattc cttaaacagg tcattatgtt gttatgatta gaagatcata | 4200 |
| gaaaagtat agatattgtt tgtttcagt aaaaaaaaaa cagcccaagg tgaaaaagga | 4260 |

```
-continued agatctattt attgatcacg ccgtagctag gcagtaaatt aacaaaagca atatttcttg    4320
ggaaatataa aagggtccaa aagctgtgat tcttcctttc tgttggggct gccaattcta    4380
tacgtacgta gctagttgaa tgaatagcta aatagctagg gttttgggat tttgtgcttt    4440
tacatttcat tagacaagtg atatgggcac ccatgatcca tcctatcaag aaaagacatt    4500
tcccaaccct cttctgtgat atttgacttt ccatatagca taggtataat gctctatcaa    4560
atcaagaact aatgaaatat acggataaag aaactaaaca ttttgctatg cctatgaaca    4620
ttggtcaaac tagggttgtt acttttcact agagaaagat aataaacgtt gcatgaaata    4680
gttgtaacaa gtaaattgat gatttttttt tgcattgcaa taaatttaca gaaaactgtg    4740
gcaacaacaa aagcagcagc agcaggagga gtggcagaat gtagagtagc agcagaaaga    4800
tggataccat tcgatgaagg agaacaaaga aggagcctat tactagctga tcaaaggaat    4860
gccacgtggc agatgatgca tttgtcttgt tcaccaccca cctccaccac cccccatcat    4920
catctcatga acatcaactc atctactgca gcaattagta atactatatc tggaactact    4980
tctccaataa tatgcagtag taatactcca tcaacaccaa gaacgacaat ggagccaaag    5040
caactcttca aaaccaaaga tcatctcaat atatttatag cacccttag aacagataat     5100 cgtaaacacg aaaatatgga aaacattgtt ggagacgaag gacaggaaga atctcagacc    5160
cttgaattgt ttcctctccg cagcagcaat gataacaacg acgataataa tttttcggag    5220
aaggatgaag tagagatatc aggggccgat gctaactcga acagtaactt tagtggtagt    5280
cattaccagt tttttgagtt tcttccactt aaaaactaag ggatctagag acagggtgct    5340
ttaatttctt agtctcttcc tatttatgta acttaaaatt aatgatggga ttttttccct    5400
attattagta atgttgtggt tcaatgatat atgtatcctt tcgggaaatc gaagattgcc    5460
gtaaatgcat ttgtatcatg tgtatgcaac gcttttacta cttatttttg ggggtaatta    5520
tgttgtagct atcgtagaaa ttctgatgtt gagagcagtt ggcctcttgt ttagccgaaa    5580
atgtcattgc tcctaaaaat taatctgact cttataaagt tgatatatat atatatacac    5640
tttttttgtg cgtaggctgg ggcgaagata                                     5670
```

METHODS AND COMPOSITIONS FOR ALTERING PLANT BIOMASS

CROSS-REFERENCE TO RELATED APPLICATIONS

This application claims the benefit of priority of U.S. Provisional Application Ser. No. 61/121,479, filed on Dec. 10, 2008, the disclosure of which is incorporated herein by reference in its entirety.

BACKGROUND OF THE INVENTION

1. Field of the Invention

The present invention relates generally to the field of molecular biology. More specifically, the invention relates to plant genes involved in plant morphology and methods of use thereof.

2. Description of the Related Art

There is a great need in the art for new genes capable of improving biomass, for example by altering leaf morphology. As the primary photosynthetic organs and sites of gaseous exchange, leaves play a crucial role for the success of land plants. Wider leaf area allows more efficient capture of solar energy and, together with thin and flat surfaces, promotes efficient gaseous exchange (Tsukaya, 2005). Although broader leaves are more efficient in terms of photosynthesis, they are not equally preferable for all environments, as this feature also exposes them to lose more water by transpiration in warm and dry areas. Plants adapted to the arid tropics, such as cactus for example, employ small and thick leaves, or perform photosynthesis in their stems, and have spines instead of leaves, to cope with the problem of dehydration. As a consequence, they grow slowly because their capacity for photosynthesis is limited by the available surface area.

Other plants, which grow mainly in tropical and subtropical environments, such as sugarcane, maize and sorghum, modify their leaves with characteristic Krantz anatomy for C4 photosynthesis. In this case, the leaves contain two interconnected but distinct cell types in which the thin-walled mesophyll cells close to the surface facilitate $CO_2$ entry whereas the thick-walled bundle sheath cells beneath the mesophyll serve as the actual sites of photosynthesis where water loss is relatively reduced. When the same species is grown under different conditions, for example, in both sun and shade, leaf morphology or arrangement of cells varies between plants grown in different environments. Leaves, therefore, maintain a wide range of plasticity in size and shape, and have adaptive significance for plants to successfully colonize a particular environment. However, little is known about the genetic determinants leaf shape and size. A gene affecting leaf shape or size could be useful for increasing biomass. The present invention provides such a gene.

SUMMARY OF THE INVENTION

In one aspect, the invention provides an isolated nucleic acid encoding a polypeptide having STF activity and which may be capable of modifying plant leaf morphology. In certain embodiments, the nucleic acid sequence may be further defined as selected from the group consisting of (a) a sequence encoding a polypeptide at least 85% identical to SEQ ID NO:2, 4, 6, 8, 10, 12 or 14, where the polypeptide modifies plant morphology and comprises a homeodomain and four motifs highly conserved with SEQ ID NO:2; (b) a sequence comprising SEQ ID NO:1, 3, 5, 7, 9, 11, 13, 15, 17, 19, 21, 23 or 25; (c) a sequence hybridizing to (b) under wash conditions of 0.15 M NaCl and 70° C. for 10 minutes, where the sequence encodes a protein that modifies plant morphology and comprises a homeodomain and four motifs highly conserved with SEQ ID NO:2; (d) a sequence comprising at least 85% sequence identity over the full length of the SEQ ID NO:1, 3, 5, 7, 9, 11, 13, 15, 17, 19, 21, 23 or 25, where the sequence encodes a protein that modifies plant morphology and comprises a homeodomain and four motifs highly conserved with SEQ ID NO:2; and (e) a sequence complementary to (a), (b), (c) or (d). In some embodiments, the isolated nucleic acid comprises the sequence of SEQ ID NO:1. In various embodiments, the isolated nucleic acid is isolated from a plant, for example M. truncatula, alfalfa, lotus, soybean, grape, poplar or tobacco.

In another aspect, the invention provides recombinant vectors comprising the above isolated nucleic acid sequences operably linked to a heterologous promoter functional in plants. In some embodiments, the vector further comprises at least one additional sequence chosen from the group consisting of: a regulatory sequence, a selectable marker, a leader sequence and a terminator. In various embodiments, the additional sequence is a heterologous sequence. In additional embodiments, the promoter is a tissue-specific promoter. In further embodiments, the promoter directs expression in leaf primordia. In additional embodiments, the recombinant vector is defined as an isolated expression cassette.

In yet another aspect, the invention provides an isolated polypeptide selected from the group consisting of: (a) a polypeptide comprising the amino acid sequence of SEQ ID NO:2, 4, 6, 8, 10, 12, 14, 16, 18, 20, 22, 24 or 26; and (b) a polypeptide having at least 85% sequence identity to SEQ ID NO:2, where the polypeptide modifies plant morphology and comprises a homeodomain and four motifs highly conserved with SEQ ID NO:2. In some embodiments, the isolated polypeptide comprises the amino acid sequence of SEQ ID NO:2.

In still another aspect, the invention provides a transgenic plant transformed with the above-described recombinant vector. In some embodiments, the plant is a dicotyledonous plant, for example a poplar, a willow, a eucalyptus, a hemp, a *Medicago* sp., a *Lotus* sp., a *Trifolium* sp., a *Melilotus* sp., a *Vinca* sp., a *Nicotiana* sp., a *Vitis* sp., a *Ricinus* sp., or a *Glycine* sp. The plant can be an $R_0$ transgenic plant. Alternatively, the plant can be a progeny plant of any generation of an $R_0$ transgenic plant, wherein the transgenic plant has the nucleic acid sequence from the $R_0$ transgenic plant.

In still yet another aspect, the invention provides a seed of a transgenic plant of the invention, wherein the seed comprises the nucleic acid sequence.

In a further aspect, the invention also provides a host cell transformed with the above-described recombinant vector. In some embodiments, the host cell is a plant cell.

In an additional aspect, the invention provides a method of altering biomass in a plant. The method comprises expressing in the plant the above-described recombinant vector, where the expression of the nucleic acid sequence alters biomass of the plant when compared to a plant of the same genotype that lacks the nucleic acid sequence. In some embodiments of this method, the recombinant vector is inherited from a parent plant of said plant. In other embodiments, the plant is directly transformed with the recombinant vector. In further embodiments, the altered biomass is increased biomass. The plant in these methods can have altered morphology when compared to a plant of the same genotype that lacks the nucleic acid sequence. An example of the altered morphology is altered leaf morphology.

In a further aspect, the invention provides a method of producing plant biomass. The method comprises (a) obtaining the above-described transformed plant; (b) growing said plant under plant growth conditions to produce plant tissue from the plant; and (c) preparing biomass from the plant tissue. Preparing biomass here can comprise harvesting the plant tissue. The biomass can be used, for example, for biofuel.

In still another aspect, the invention provides a plant genetically engineered to reduce or eliminate expression of an STF, where the STF comprises SEQ ID NO:2, 4, 6, 8, 10, 12, 14, 16, 18, 20, 22, 24 or 26, or a sequence at least 85% identical to SEQ ID NO:2, 4, 6, 8, 10, 12, 14, 16, 18, 20, 22, 24 or 26, where the polypeptide modifies plant morphology and comprises a homeodomain and four motifs highly conserved with SEQ ID NO:2. In some embodiments, the expression of the STF is reduced or eliminated by a heterologous nucleic acid having homology to the STF, for example an antisense, a ribozyme or a miRNA, or a nucleic acid encoding an RNA that causes RNAi against STF, including but not limited to a siRNA. In other embodiments, the expression of the STF is eliminated by an insertion in the STF gene. The plant of these aspects can be, for example, a dicotyledonous plant such as a poplar, a willow, a eucalyptus, a hemp, a *Medicago* sp., a *Lotus* sp., a *Trifolium* sp., a *Melilotus* sp., a *Vinca* sp., or a *Glycine* sp.

In another embodiment, the present invention provides an isolated nucleic acid sequence that has promoter activity. The nucleic acid sequence with promoter activity can comprise SEQ ID NO:28 or 29, or a fragment of at least 95 contiguous nucleotides thereof with promoter activity. The nucleic acid sequence with promoter activity can be an isolated nucleic acid sequence having at least 90% sequence identity to the nucleic acid sequence of SEQ ID NO:28 or 29, wherein the isolated nucleic acid sequence has promoter activity.

In a some aspects, the isolated nucleic acid having promoter activity can be further defined as operably linked to a heterologous transcribable polynucleotide sequence. In some aspects, the isolated nucleic acid having promoter activity can comprise a fragment of at least 125, 250, 400, or 500 or more contiguous nucleotides of SEQ ID NO:28 or SEQ ID NO:29, including the full length of the sequence, wherein the fragment has promoter activity.

In further embodiments, the present invention provides a plant transformed with a selected DNA comprising the promoter sequence of SEQ ID NO:28 or SEQ ID NO:29, or a fragment thereof. The present invention also provides a cell or a seed of the plant comprising the promoter sequence of SEQ ID NO:28 or SEQ ID NO:29, or a fragment thereof.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIGS. 6A-6C: STF homology to STL (STF-like sequences in other plants) and phylogenetic relationship to the closest WOX proteins. A: STF gene structure with four exons. Upper panel: STF gene structure (SEQ ID NO:1) showing the position of the Tnt1 insertion site (arrows) in the six alleles. Lower panel: The homologous NsSTL1 gene (SEQ. ID NO:19) from *Nicotiana sylvestris* with similar exon-intron structure representing STF-like genes (STLs). B: Full-length amino acid alignment of STL (STF-like) proteins from *Nicotiana benthamiana* ("NbSTL1"; SEQ ID NO:14); *Nicotiana sylvestris* ("NsSTL1"; SEQ ID NO:20); *Medicago truncatula* ("STF"; SEQ ID NO:2); *Medicago sativa* ("MsSTL1"; SEQ ID NO:4); *Glycine max* ("GmSTL1"; SEQ ID NO:8); *Lotus*

Figure 1:
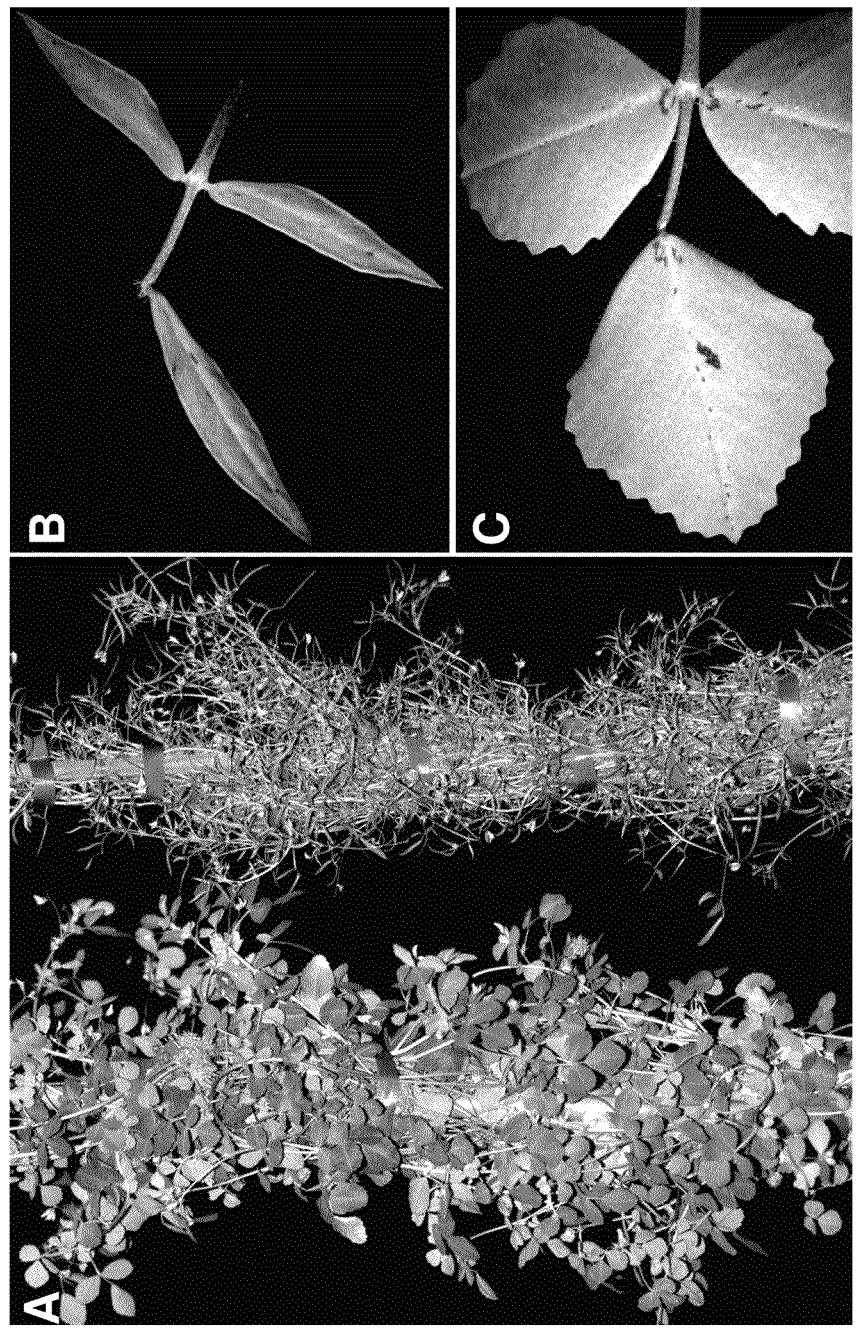
FIG. 1: The stf mutant of *Medicago truncatula* is severely impaired in leaf lamina expansion. A: adult stf mutant (right) and wild-type R108 (left). The stf mutant grows to the same height and flowers at about the same time as the wild-type, but sets no pods. B: Leaves of the stf mutant maintain trifoliate identity with normal proximodistal growth, but mediolateral (lamina) expansion is arrested leading to rod-shaped leaves with pointed tips. C: Wild-type R108 control. D: Stems of the stf mutant (right) are thinner than wt stems (left). E: Bar graph showing total above-ground biomass produced by adult plants expressed as dry weight per plant. The wild-type produced on average 2.5-fold more biomass than the mutant under standard greenhouse conditions.

*japonicus* ("LjSTL1": SEQ ID NO:6); *Vitis vinifera* ("VvSTL1": SEQ ID NO:10): *Ricinus cummunis* ("Rc-STL1"; SEQ ID NO:24); and *Populus trichocarpa* ("PtSTL1"; SEQ ID NO:12). There is strong homology throughout and especially at four highly conserved motifs outside the homeodomain including the last ten amino acids. C: Phylogenetic tree showing the relationship between STF, STL and the closest WOX homeodomain proteins based on percentage amino acid identity. The closest *Arabidopsis* STF homologue, AtWOX1, is more distantly related to STF than the six STL identified herein, suggesting that STF and STL form a separate sub-class of WOX related proteins with specific functions.

FIG. 7: In situ localization of STF transcript. A: STF expression in vegetative shoot apex. STF is weakly expressed in a few cells in incipient and young primordia in the adaxial side. In older primordia, expression shifts to the central region and appears patchy in more cells. B: Negative control with a sense probe. C: STF expression in floral apex. Expression is even weaker than in the shoot apex but still detected in the floral primordia and petaloid organs rather than in the floral meristem. D: Positive control for floral apex using PIM probe expressed in floral organs.

FIG. 8: Identification of NsSTL1 deletion in lam1 mutant and complementation of lam1. A: Adult lam1 mutant plant. B: Comparable adult leaves from wild-type *N. sylvestris* (left) and lam1 mutant (right). C: Deletion of the NsSTL1 locus in the lam1 mutant verified by RT-PCR. Three lam1 and three wild-type plants were used for RNA extraction and reverse transcription. A 1.2 kb NsSTL1 transcript was detected in all the wild-type but not in the mutant using NsSTL1 specific primers. The tobacco actin gene was used as control for loading and RNA integrity. D: Deletion of the NsSTL1 locus in the lam1 mutant verified by genomic PCR. Various primer pair combinations spanning the full-length NsSTL1 gene and the upstream 2.46 kb region of the promoter amplified the expected fragment from wild-type but none from the lam1 mutant. The primer pair F1/R1 amplifies most of the NsSTL1 coding sequence (CDS) region, the primer pair F1/R2 amplifies the coding sequence and 3' UTR, and the primer pair F2/R3 amplifies the promoter, the 5' UTR plus part of the coding sequence, and together span 5.67 kb of the NsSTL1 region. E: Untransformed *N. sylvestris* plant regenerated from wild-type leaf via somatic embryogenesis. F: lam1 mutant complemented with 5.18 kb genomic STF fragment from *M. truncatula*.

DESCRIPTION OF SEQUENCE LISTING

SEQ ID NO:1—nucleotide sequence of STF encoding STF1 as shown in FIG. 6B.
SEQ ID NO:2—amino acid sequence of STF1 as shown in FIG. 6B
SEQ ID NO:3—nucleotide sequence of alfalfa STL encoding MsSTL1 of FIG. 6B starting at amino acid 14 of MsSTL.
SEQ ID NO:4—amino acid sequence of MsSTL1 as shown in FIG. 6B
SEQ ID NO:5—nucleotide sequence of lotus STL encoding LjSTL1 of FIG. 6B
SEQ ID NO:6—amino acid sequence of LjSTL1 as shown in FIG. 6B
SEQ ID NO:7—nucleotide sequence of soybean STL encoding GmSTL1 of FIG. 6B
SEQ ID NO:8—amino acid sequence of GmSTL1 as shown in FIG. 6B
SEQ ID NO:9—nucleotide sequence of grape STL encoding VvSTL1 of FIG. 6B
SEQ ID NO:10—amino acid sequence of VvSTL1 as shown in FIG. 6B
SEQ ID NO:11—nucleotide sequence of poplar STL encoding PtSTL1 of FIG. 6B
SEQ ID NO:12—amino acid sequence of PtSTL1 as shown in FIG. 6B
SEQ ID NO:13—nucleotide sequence of tobacco STL encoding NbSTL1 of FIG. 6B
SEQ ID NO:14—amino acid sequence of NbSTL1 as shown in FIG. 6B
SEQ ID NO:15—nucleotide sequence of soybean STL2, not including stop codon, encoding GmSTL2
SEQ ID NO:16—amino acid sequence of GmSTL2
SEQ ID NO:17—nucleotide sequence of *Medicago sativa* STL2 encoding MsSTL2
SEQ ID NO:18—amino acid sequence of MsSTL2
SEQ ID NO:19—nucleotide sequence of *Nicotiana sylvestris* STL1 encoding NsSTL1 (identified as NsLAM1 herein)
SEQ ID NO:20—amino acid sequence of NsSTL1
SEQ ID NO:21—nucleotide sequence of *Populus trichocarpa* STL2 encoding PtSTL2
SEQ ID NO:22—amino acid sequence of PtSTL2
SEQ ID NO:23—nucleotide sequence of *Ricinis communis* STL1 encoding RcSTL1
SEQ ID NO:24—amino acid sequence of RcSTL2
SEQ ID NO:25—nucleotide sequence of *Vitis vinifera* STL2 encoding VvSTL2
SEQ ID NO:26—amino acid sequence of VvSTL2
SEQ ID NO:27—amino acid sequence of PhMAW
SEQ ID NO:28—nucleotide sequence of the STF locus including the promoter, 5'UTR, introns, exons, and 3'UTR.
SEQ ID NO:29—nucleotide sequence of the NsSTL1 locus including the promoter, 5'UTR, introns, exons, and 3'UTR.

DETAILED DESCRIPTION OF THE INVENTION

Figure 4:
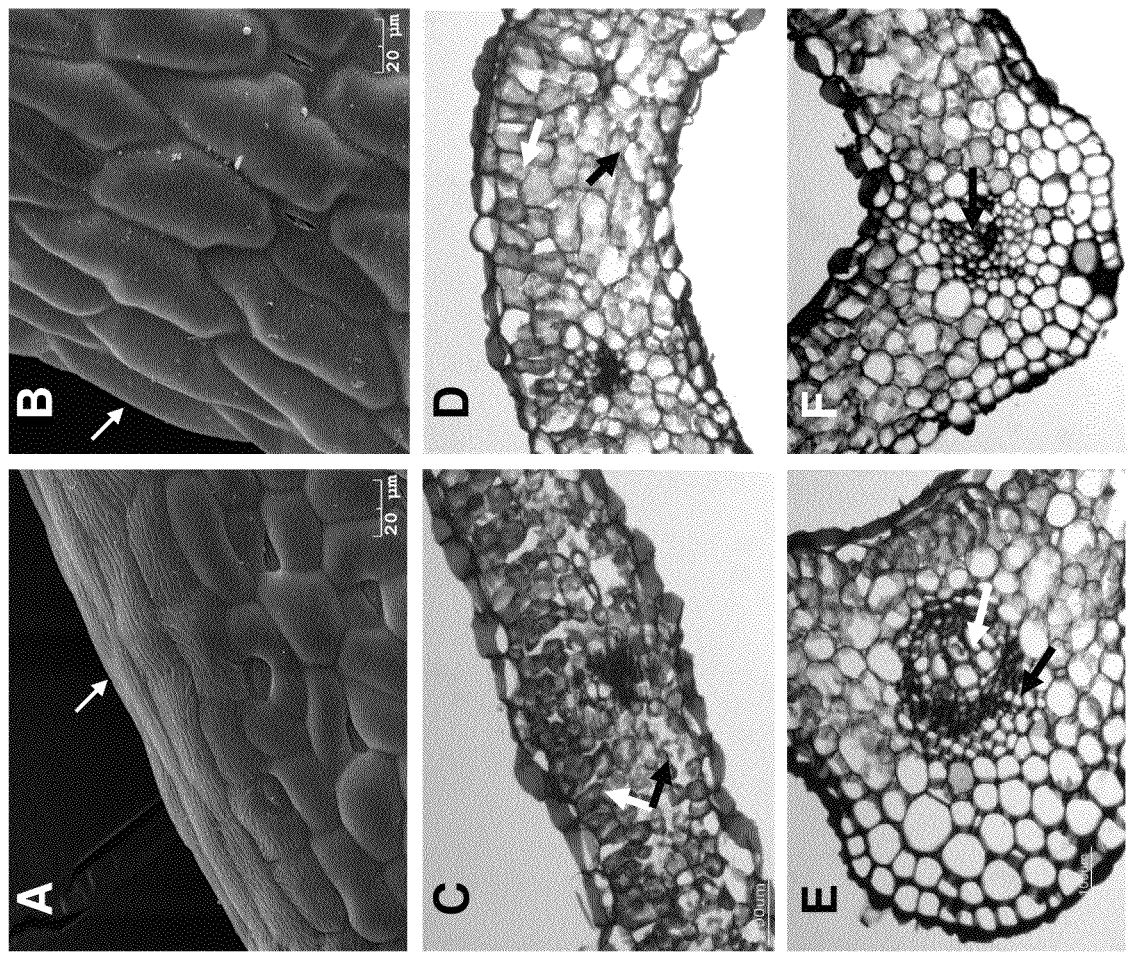
FIG. 4: Leaves of the stf mutant lack marginal elongated cells and adaxial cell types. A and B: Scanning electron microscope view of leaf epidermal cells. Epidermal cells of the stf mutant (B) are generally longer than wild-type (A) but typical marginal files of elongated cells are missing in the mutant (arrow). C and D: Transverse section through wild-type (C) and stf (D) leaf. In the wild-type leaf, palisade mesophyll cells (white arrow) are adaxial and cylindrical in shape, whereas spongy mesophyll cells (black arrow) are abaxial with irregular shape; the two cell types are clearly distinguishable. In the stf mutant (D), adaxial palisade mesophyll cells (white arrow) are compact and variable in shape and are indistinguishable from abaxial spongy mesophyll cells (black arrow). E and F: Transverse section through the midvein of wt (E) and stf (F) leaf The midvein of the wild-type is well differentiated into xylem vessels (white arrow) in the adaxial side and phloem vessels in the abaxial side (black arrow). The vasculature is poorly differentiated in the mutant and xylem cells look like phloem cells (black arrow). Leaf sections in C-F were stained with toludine blue.

The invention overcomes the limitations of the prior art by providing plant genes (STF and STL) that affect leaf morphology. In certain embodiments, such sequences affect lamina development, in particular lamina expansion and polarity. Plants not expressing either STF or STL may exhibit arrested leaf and petal lamina expansion, such that a narrow lamina with a grass-like structure results. STF is provided herein as SEQ ID NO:1, with the encoded protein (STF or STF1) as SEQ ID NO:2. It is believed that STL genes (examples provided as SEQ ID NO:1, 3, 5, 7, 9, 11, 13, 15, 17, 19, 21, 23 or 25 encoding SEQ ID NO:2, 4, 6, 8, 10, 12, 14, 16, 18, 20, 22, 24 or 26 respectively) are orthologues of STF, by virtue of their very similar structure, in particular the presence of a highly conserved homeodomain, at amino acid residues as indicated by bar number 1 in the alignment in FIG. 6B, and 4 highly conserved motifs, indicated by bars 2-5 above the sequence alignments in FIG. 6B. In recognition of their homology, similar structure, and likely same activity, STL genes or STL polypeptides may also be referred to herein as having STF activity.

Because knockout insertion mutants of STF have greatly reduced biomass, one embodiment of the invention concerns overexpression of STF or STL to produce plants with increased biomass. Therefore, in accordance with the invention, leaf morphology and biomass production can be influenced by over-expression or down-regulation of STF or STL.

I. Nucleic Acids, Polypeptides and Plant Transformation Constructs

Certain embodiments of the current invention concern isolated nucleic acid sequences comprising a STF or STL coding sequence. Exemplary coding sequences for use with the invention include SEQ ID NO:1, 3, 5, 7, 9, 11, 13, 15, 17, 19, 21, 23 or 25 encoding the polypeptides of SEQ ID NO:2, 4, 6, 8, 10, 12, 14, 16, 18, 20, 22, 24 or 26, respectively.

Additional embodiments of the current invention concern isolated nucleic acids sequences comprising a STF or STL promoter sequence. SEQ ID NO: 28 comprises the genomic STF locus, including promoter, 5'UTR, introns, exons and 3'UTR. SEQ ID NO:29 comprises the genomic NsSTL1 including promoter, 5'UTR, introns, exons and 3'UTR.

The invention provides a nucleic acid sequence identical over its entire length to each coding sequence provided herein. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro- protein sequence. The nucleic acid can also include non-coding sequences, including for example, but not limited to, non-coding 540 and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Nucleic acids of the present invention also include nucleic acids comprising a structural gene and the naturally associated sequences that control gene expression.

Another aspect of the present invention relates to the polypeptide sequences provided herein, as well as polypeptides and fragments thereof, particularly those polypeptides that exhibit STF activity and also those polypeptides that have at least 85% identity, more preferably at least 90% identity, and most preferably at least 95% identity to a polypeptide sequence selected from the group of sequences set forth herein, and also include portions of such polypeptides, wherein such portion of the polypeptide preferably includes at least 30 amino acids and more preferably includes at least 50 amino acids.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk, ed., (1988); Smith, ed., (1993); Griffin, and Griffin, eds., (1994); von Heinje, (1987); Gribskov and Devereux, eds., (1991); and Carillo and Lipman, (1988). Computer programs can be used to determine "identity" between two sequences these programs include but are not limited to, GCG (Devereux, 1984); suite of five BLAST programs, three designed for nucleotide sequences queries (BLASTN, BLASTX, and TBLASTX) and two designed for protein sequence queries (BLASTP and TBLASTN) (Coulson, 1994; Birren, et al., 1997). The BLASTX program is publicly available from NCBI and other sources (BLAST Manual, Altschul, S., et al., NCBI NLM NIH, Bethesda, Md. 20894; Altschul, S., et al., 1990). The well known Smith Waterman algorithm can also be used to determine identity.

Parameters for polypeptide sequence comparison include the following: Algorithm: Needleman and Wunsch (1970); Comparison matrix: BLOSUM62 from Hentikoff and Hentikoff, (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for nucleic acid sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

It is further recognized that a polypeptide at least 85%, 90%, 92%, 95%, or 98% identical to SEQ ID NO:2, 4, 6, 8, 10, 12, 14, 16, 18, 20, 22, 24 or 26 that is an STF or STL (i.e., modifies plant morphology, especially leaf expansion or polarity) could be readily identified as such by the skilled artisan by comparison of the polypeptide sequence with SEQ ID NO:2, 4, 6, 8, 10, 12, 14, 16, 18, 20, 22, 24 or 26, since the sequences provided in the Examples establish regions having conserved or identical amino acid sequences, which would be expected to also be conserved in an orthologue to retain activity. In particular, an active STF or STL is expected to have a homeodomain and four motifs highly conserved with SEQ ID NO:2, where the homeodomain is at amino acid residues indicated by bar 1 on the sequence alignment in FIG. 6B and the four highly conserved motifs are at residues indicated by bars 2-5 as aligned in FIG. 6B. Other areas where amino acid residues are conserved or identical can be identified without undue experimentation in FIG. 6B, further pointing out residues that are likely to be important for activity. Further, nucleic acid sequences encoding STF or STL can be identified without undue experimentation by determining the encoded amino acid sequence and comparing that amino acid sequence with the nine sequences provided in FIG. 6B.

Provided herein are also nucleic acids capable of hybridizing to the nucleic acid sequences identified herein, for example, of SEQ ID NO:1, 3, 5, 7, 9, 11, 13, 15, 17, 19, 21, 23 or 25. As used herein, "hybridization," "hybridizes" or "capable of hybridizing" is understood to mean the forming of a double- or triple-stranded molecule or a molecule with partial double- or triple-stranded nature. Such hybridization may take place under relatively high-stringency conditions, including low salt and/or high temperature conditions, such as provided by a wash in about 0.02 M to about 0.15 M NaCl at temperatures of about 50° C. to about 70° C. for 10 min. In embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like. In some embodiments, the sequence encodes a protein that modifies plant morphology and comprises a homeodomain and four motifs highly conserved with SEQ ID NO:2, as discussed above.

Complements to any of the above-described nucleic acid sequences are also provided.

The nucleic acids provided herein can be from any source, e.g., identified as naturally occurring in a plant, or synthesized, e.g., by mutagenesis of known sequences SEQ ID NO:1, 3, 5, 7, 9, 11, 13, 15, 17, 19, 21, 23 or 25, or sequences encoding SEQ ID NO:2, 4, 6, 8, 10, 12, 14, 16, 18, 20, 22, 24 or 26. Where naturally occurring in a plant, the invention contemplates a naturally occurring sequence from any plant. In some embodiments, the plant is a dicotyledonous plant, for example a poplar, a willow, a eucalyptus, a hemp, a *Medicago* sp., a *Lotus* sp., a *Trifolium* sp., a *Melilotus* sp., a *Vinca* sp., a *Nicotiana* sp., a *Vitis* sp., a *Ricinus* sp., or a *Glycine* sp.

Coding sequences may be provided in a recombinant vector operably linked to a heterologous promoter functional in plants, in either sense or antisense orientation. Expression constructs are also provided comprising these sequences, including antisense oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

The choice of any additional elements used in conjunction with the STF or STL coding sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to, e.g., an entire biosynthetic pathway, into a plant.

Particularly useful for transformation are expression cassettes which have been isolated from such vectors. DNA segments used for transforming plant cells will generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current invention are as follows.

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), α-tubulin, actin (Wang et al., 1992), cab (Sullivan et al., 1989), PEPCase (Hudspeth and Grula, 1989) or those promoters associated with the R gene complex (Chandler et al., 1989). Tissue-specific promoters such as leaf specific promoters, or tissue selective promoters (e.g., promoters that direct greater expression in leaf primordia than in other tissues), and tissue-specific enhancers (Fromm et al., 1986) are also contemplated to be useful, as are inducible promoters such as ABA- and turgor-inducible promoters. In one embodiment of the invention, the CaMV35S promoter is used to express STF or STL coding sequences.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that STF or STL coding sequences may be introduced under the control of novel promoters, enhancers, etc., or homologous or tissue-specific or tissue-selective promoters or control elements. Vectors for use in tissue-specific targeting of genes in transgenic plants will typically include tissue-specific or tissue-selective promoters and may also include other tissue-specific or tissue-selective control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots.

B. Terminators

Transformation constructs prepared in accordance with the invention will typically include a 3' end DNA sequence that acts as a signal to terminate transcription and allow for the polyadenylation of the mRNA produced by coding sequences operably linked to a promoter. In one embodiment of the invention, the native terminator of a STF or STL coding sequence is used. Alternatively, a heterologous 3' end may enhance the expression of sense or antisense STF or STL coding sequences. Examples of terminators that may be used in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II gene from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene products by protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed.

D. Marker Genes

By employing a selectable or screenable marker, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

One beneficial use of the sequences provided by the invention will be in the alteration of plant phenotypes by genetic transformation with STF or STL coding sequences. The STF or STL coding sequence may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

II. Genetic Transformation

Additionally provided herein are transgenic plants transformed with the above-identified recombinant vector encoding an STF or STL, or a sequence modulating down-regulation thereof.

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, including alfalfa (Thomas et al., 1990), it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. Gateway™ and other recombination-based cloning technology is also available in vectors useful for plant transformation. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

The transgenic plants of the present invention expressing heterologous STF and STL can be of any species. In some embodiments, the transgenic plant is a dicotyledonous plant, for example a plant used in biomass and forage crop production such as a poplar, a willow, a eucalyptus, a hemp, a *Medicago* sp., a *Lotus* sp., a *Trifolium* sp., a *Melilotus* sp., a *Vinca* sp., a *Nicotiana* sp., a *Vitis* sp., a *Ricinus* sp., or a *Glycine* sp. The plant can be an $R_0$ transgenic plant (i.e., a plant derived from the original transformed tissue). The plant can also be a progeny plant of any generation of an $R_0$ transgenic plant, wherein the transgenic plant has the nucleic acid sequence from the $R_0$ transgenic plant.

Seeds of the above-described transgenic plant are also contemplated, particularly where the seed comprises the nucleic acid sequence. Additionally contemplated are host cells transformed with the above-identified recombinant vector. In some embodiments, the host cell is a plant cell.

Also contemplated herein is a plant genetically engineered to reduce or eliminate expression of an STF (e.g., an STF "knockout"), where the STF comprises SEQ ID NO:2, 4, 6, 8, 10, 12, 14, 16, 18, 20, 22, 24 or 26, or a sequence at least 85%, 90%, 92%, 95%, or 98% identical to SEQ ID NO:2, 4, 6, 8, 10, 12, 14, 16, 18, 20, 22, 24 or 26, where the polypeptide modifies plant morphology and comprises a homeodomain and four motifs highly conserved with SEQ ID NO:2. Such plants are described in the Example, and may be useful, e.g., as ornamental plants, due to their unusual leaf and flower morphology.

In these embodiments, expression of the STF can be reduced or eliminated by any known method, for example by introducing a heterologous nucleic acid having homology to the STF into the plant. In specific embodiments, methods and plants produced thereby are provided in which all or a portion of a sequence complementary to a nucleic acid provided herein is expressed in a plant cell to result down-regulation of the activity of the corresponding encoded polypeptide. Further nonlimiting examples of such heterologous nucleic acids include an antisense, a ribozyme or a miRNA, as they are known in the art.

The expression of the STF may also be eliminated by an insertion in the STF gene, e.g. as in the Example, where the retrotransposon Tnt1 was inserted into the STF gene.

The plants of these embodiments having reduced or eliminated expression of STF can be of any species. In some embodiments, the plant is a dicotyledonous plant, e.g., a poplar, a willow, a eucalyptus, a hemp, a *Medicago* sp., a *Lotus* sp., a *Trifolium* sp., a *Melilotus* sp., a *Vinca* sp., or a *Glycine* sp.

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. A medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. The rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce, into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad-spectrum herbicide bialaphos. Another example of a herbicide which is useful for selection of transformed cell lines in the practice of the invention is the broad-spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived therefrom. U.S. Pat. No. 4,535,060 describes the isolation of EPSPS mutations which confer glyphosate resistance on the EPSPS of *Salmonella typhimurium*, encoded by the gene aroA. The EPSPS gene from *Zea mays* was cloned and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $M^{-2}$ $s^{-1}$ of light. Plants may be matured in a growth chamber or greenhouse. Plants can be regenerated in from about 6 weeks to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Evaluation of Biomass Production

As previously discussed, overexpression of STF or STL is expected to provide a plant that has increased biomass production. Thus, a method of altering biomass in a plant is provided. The method comprises expressing in the plant the above-identified recombinant vector comprising an STF coding region, where the expression of the nucleic acid sequence alters the biomass of the plant when compared to a plant of the same genotype that lacks the nucleic acid sequence. In these embodiments, the plant can be the $R_0$ transgenic plant. Alternatively, the plant can be a progeny plant of any generation of an $R_0$ transgenic plant, where the transgenic plant has the nucleic acid sequence from the $R_0$ transgenic plant.

In some of these embodiments, the plant has altered morphology when compared to a plant of the same genotype that lacks the nucleic acid sequence. An example of altered morphology that can be observed in the plants of these methods is altered leaf morphology.

The plants overexpressing STF can also be used to produce plant biomass, for example by obtaining the above-identified plant expressing a heterologous STF, growing said plant under plant growth conditions to produce plant tissue from the plant; and preparing biomass from said plant tissue. The biomass can be subsequently used for any purpose, for example to produce biofuel.

V. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected STF or STL coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein, the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a plant of a starting line with a plant of a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. Definitions

Expression: The combination of intracellular processes, including transcription and translation, undergone by a coding DNA molecule such as a structural gene to produce a polypeptide.

Genetic Transformation: A process of introducing a DNA sequence or construct (e.g., a vector or expression cassette)

into a cell or protoplast in which that exogenous DNA is incorporated into a chromosome or is capable of autonomous replication.

Heterologous: A sequence which is not normally present in a given host genome in the genetic context in which the sequence is currently found. In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell in which the DNA complement has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Identification of the STENOFOLIA Mutant in *M. truncatula*

In an effort to develop an insertion mutant resource for legume functional genomics, the tobacco retrotransposon Tnt1 was used to tag the genome of the model legume *Medicago truncatula*. *M. truncatula* is a very close relative of the important forage legume, *Medicago sativa* (alfalfa). Using Tnt1 as an insertional mutagen, approximately 10,000 independent lines were generated via somatic embryogenesis (Tadege et al., 2008). To better understand the molecular nature of the dicot leaf lamina development pathway and enable genetic manipulation of lamina size, *M. truncatula* Tnt1 lines were screened for leaf blade mutants. Visual screening of 5000 $R_1$ lines for altered leaf lamina resulted in six nearly identical mutant phenotypes, in which leaves are drastically affected in their laminal expansion in the mediolateral axis and in their dorsoventral polarity.

In all six mutant lines NF0075, NF0120, NF1345, NF1638, NF3103, and NF4710, the leaf phenotypes co-segregated as a single recessive locus in a Mendelian fashion. The most obvious phenotype of the mutation is a severe reduction of lamina expansion; as a result leaves appear very narrow and pointed (FIG. 1B). Because of this major phenotype, the mutant was named stenofolia, stf, (derived from the Greek term stenos which means narrow). The various mutant lines were designated with stf1 followed by numbers starting with stf1-1 for NF0075, stf1-2 for NF0120 and so on. Under greenhouse conditions the stf mutant grows almost like wild-type (though stems are thinner), the adult plant attaining about same height as the wild-type, but with a grass-like appearance due to the narrow leaves (FIG. 1A, right panel).

As shown in FIG. 1B and C, leaf expansion in the proximodistal axis appears to be unaffected as the length of the stf leaf is comparable to that of the wild-type. Mutant leaves also maintain trifoliate identity except on rare occasions where bifoliate and unifoliate leaves appear spontaneously. The stf mutant also developed thinner stems compared to the wild-type (FIG. 1D) suggesting an overall underperformance in above-ground tissue formation and maintenance. Because the stf leaves are very narrow, it was anticipated that the mutant will have reduced capacity to capture solar energy for photosynthesis which will impact total biomass production. To evaluate this effect, total above-ground biomass produced by the mutant was measured and compared with that of the wild-type. As shown in FIG. 1E, the wild-type plant produced at least 2.5-fold more total aerial biomass than the mutant on a dry weight basis. This suggests that the STF gene is required for biomass accumulation, which is vital for overall plant performance but particularly of paramount importance for forage and lignocellulosic biofuel crops.

Figure 2:
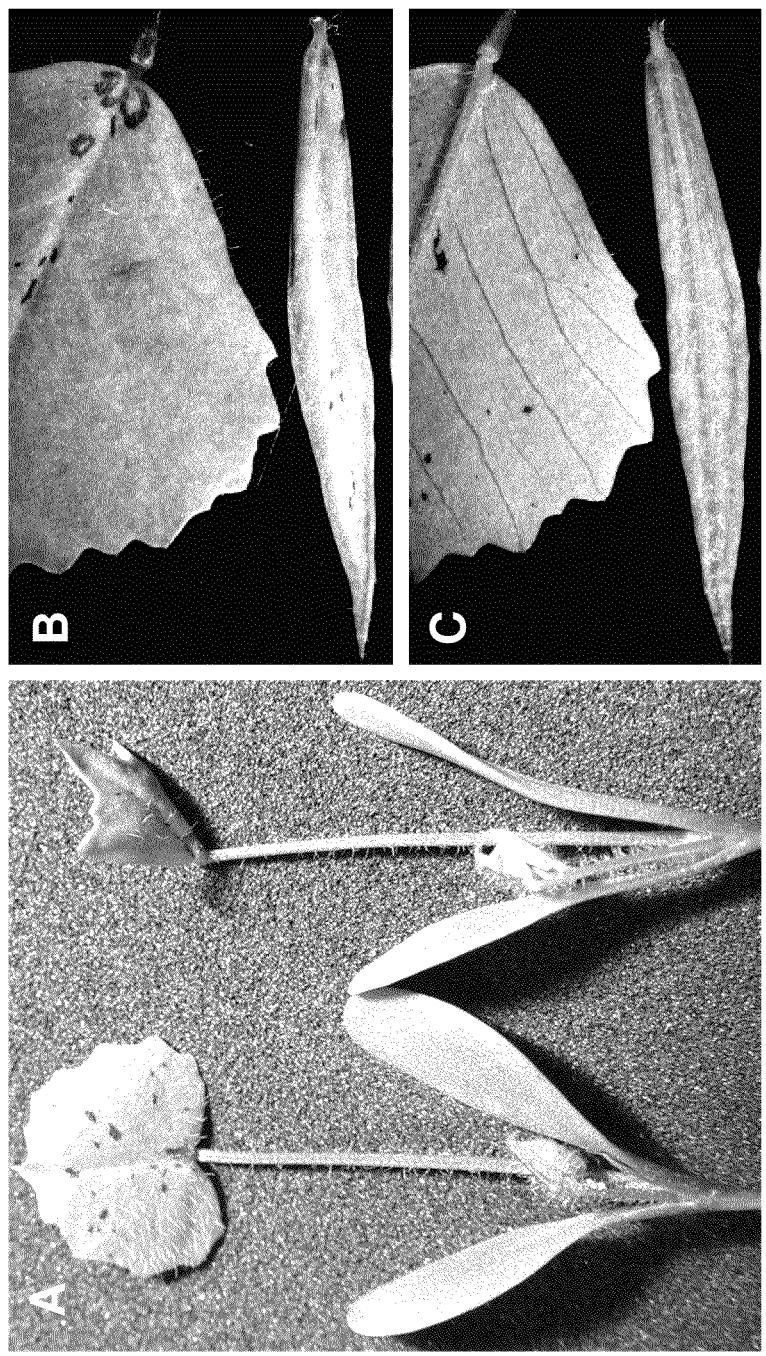
FIG. 2: The effect of stf is developmentally regulated. A: Wild-type (left) and stf (right) seedlings at the unifoliate stage. Mutant cotyledons are nearly wild-type and the stf unifoliate leaf is only partially affected in lateral expansion near the distal tip. B: Adaxial leaf surfaces of wild-type (upper) and stf leaf (lower) at maturity. C: Abaxial surfaces of leaves in B. Note that wild-type leaf surfaces in B and C are very distinct with prominent veins at the abaxial surface unlike stf. Lamina formation and venation are initiated but further development is arrested in stf.

The stf phenotype is developmentally regulated in the sense that the phenotype becomes apparent at the unifoliate stage and gets stronger as the plant grows. Mutant cotyledons are indistinguishable from wild-type and the unifoliate leaf is only partially affected (FIG. 2A). The stf unifoliate leaf starts to expand at the proximal side but expansion is arrested halfway towards the distal end resulting in a unique (kite-like) shape (FIG. 2A, right). The stf leaf at this stage has clearly distinguishable adaxial and abaxial surfaces but there seems to be unequal growth and as a result the unifoliate leaf is more curled right angle at the blade and petiole junction on the adaxial side, and, at the margins, curled towards the abaxial side (FIG. 2A, right). The wild-type unifoliate leaf is oval in shape with a very flat surface (FIG. 2A, left). The first stf trifoliate leaf appears rod-shaped, clearly different from wild-type. In this trifoliate and subsequent leaves, expansion of the lamina in the lateral plane is initiated but progressively arrested as growth ensues for the next three or four trifoliate leaves. As a result, the first trifoliate leaf appears broader than the second and the second slightly broader than the third, but after the fourth or fifth trifoliate leaf, all leaves develop a uniformly thin lamina. In the adult plant, the stf leaf is not fully radially symmetric but the difference between adaxial/dorsal and abaxial/ventral surfaces becomes drastically reduced compared to the wild-type (FIG. 2B and C). The midvein is less distinct and lateral veins are not visible on the abaxial side of stf leaf (FIG. 2C).

Figure 3:
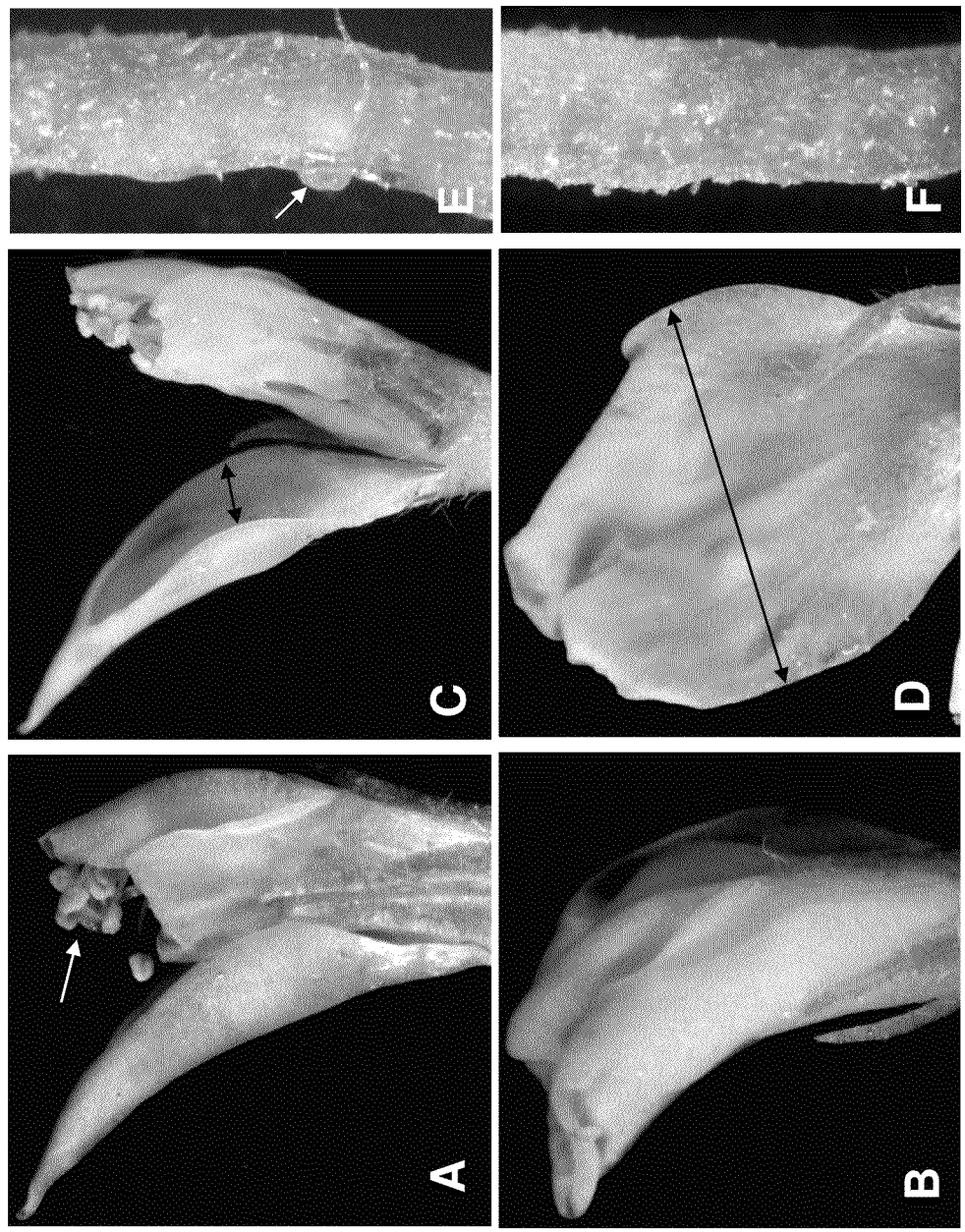
FIG. 3: The stf gene alters petal and ovary development. A: Representative whole flower of stf in which anthers and stigma are exposed early (arrow). B: Wild-type flower at the same stage as A, in which the anthers and stigma are enclosed within the petals. C: The outer petal (double arrow) of stf is drastically reduced in width compared to wild-type shown in D. E: Unlike wild-type, the stf ovary wall fails to close at the adaxial side and ovules protrude out (arrow). F: wild-type ovary wall same stage as in E.

The stf mutant plant flowers at about the same time as the wild-type, but it is completely sterile and makes no pods. The anthers and stigma in stf are exposed early to the atmosphere whereas in the wild-type they remain enclosed by petals until after pollination (FIG. 3A and B). This is caused by the inability of the outer petal to expand in the lateral plane analogous to the defect in leaf lamina expansion (FIG. 3C and D). The pollen grains look normal, but pollen viability is reduced in stf due to exposure to the relatively low humidity of the external environment. The stf carpel however is severely affected. The ovary wall fails to close on the adaxial side and ovules protrude outside of the ovary in the mutant opposed to the wild-type (FIG. 3E and F) and as a result all stf mutants do not form pods.

Examination of leaf epidermal surfaces with scanning electron microscopy showed that epidermal cells in stf are more cylindrical and longer in size whereas wild-type cells are shorter and of variable shape. Furthermore, characteristic files of elongated marginal cells are absent in the stf leaf edge (FIG. 4A and B). The stf leaf edge instead is thick and looks as if it is folded.

A transverse section through the leaf revealed that adaxial cell types are missing in the mutant. In the wild-type leaf, the cells in the palisade mesophyll layer, immediately next to the upper epidermis, are uniformly cylindrical in shape whereas cells in the spongy mesophyll, immediately next to the lower epidermis, are compact and irregular in shape (FIG. 4C). This adaxial-abaxial cellular differentiation is not apparent in the mutant in which cells on both sides are compact and look like the spongy mesophyll cells (FIG. 4D). Prominent air spaces which are common among the palisade and spongy cells of the wild-type are also absent especially from the palisade mesophyll region of the mutant.

Light microscopy examination of transverse sections through the midvein region showed that the midvein is poorly developed in the mutant. In the wild-type the midvein is well developed and differentiated into xylem vessels on the adaxial side and phloem vessels on the abaxial side (FIG. 4E). In the mutant, however, the vasculature of the midvein is reduced in size and hardly differentiated into xylem and phloem vessels (FIG. 4F). Xylem cells are practically absent in the adaxial side and replaced with phloem-like cells indicating that the stf mutation globally affects adaxial cell types. These results together suggest that the STF gene is required for adaxial cell fate throughout development and in doing so STF regulates proper lateral expansion in leaf lamina, leaf venation, petal lobes, and carpel development.

Example 2

Cloning of the STF Gene

Figure 5:
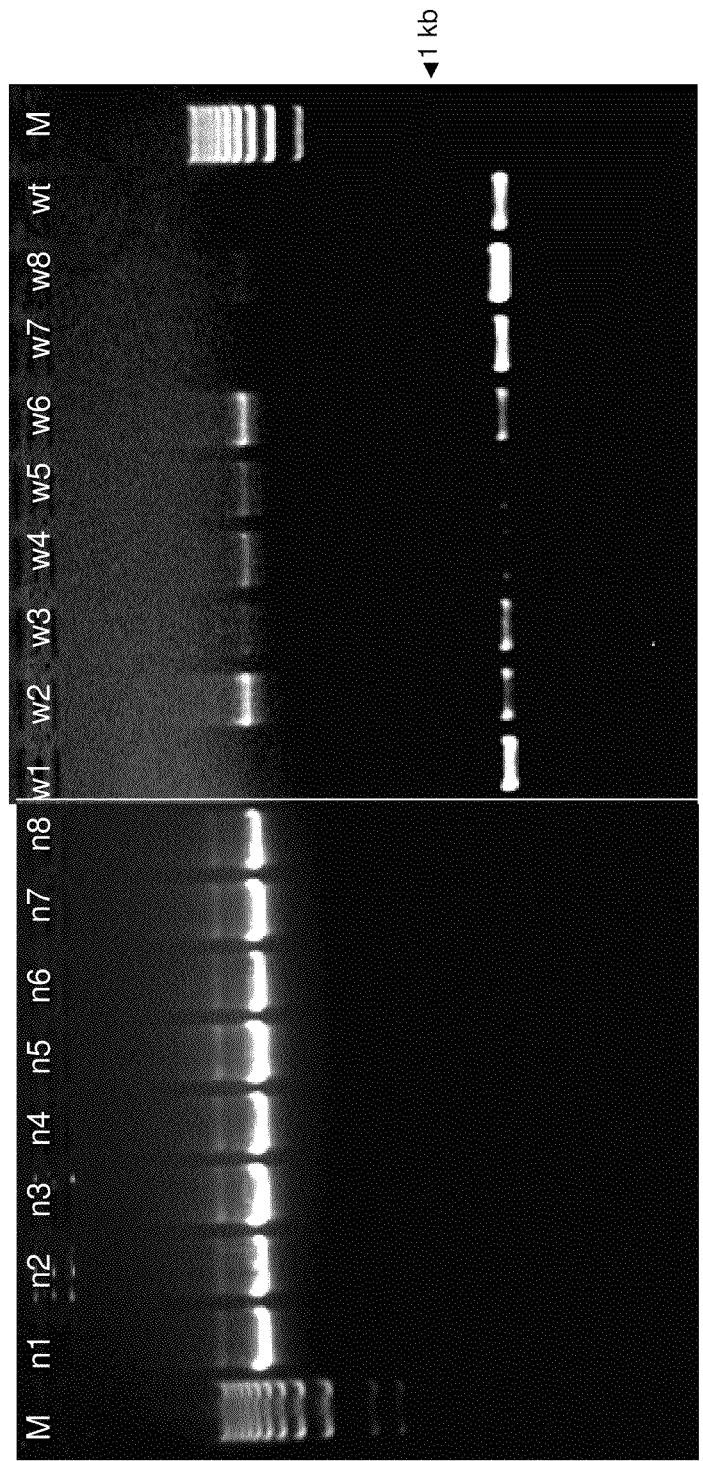
FIG. 5: Segregation analysis of Tnt1 insertion in the STF gene in R1 progenies using PCR. DNA from segregating NF0075 population was PCR amplified using STF-specific primers. All stf mutants amplified a ~6 kb band (n1-n8) showing that the 5.3 kb Tnt1 element was inserted in the STF gene. All phenotypically wild-type progeny (w1-w8) amplified a ~700 bp fragment corresponding to the wild-type, some with an additional band at ~6 kb (w2, w3, w4, w5, w6, w8). n1-n8 are homozygous for the Tnt1 insert whereas w2, w3, w4, w5, w6, heterozygous, indicating that the stf mutation is recessive.

The STF gene was cloned by a PCR-based approach using the Tnt1 tag in a population segregating for the stf phenotype. stf segregates as a single recessive mutation in all of six independent lines. After the segregation pattern was established, the Tnt1 flanking sequence tags (FSTs) was amplified and sequenced in one of the stf mutants using thermal asymmetric interlaced polymerase chain reaction (TAIL PCR). Then, by designing two FST specific primers, one inside the Tnt1 transposon, and one in the flanking genomic DNA identified in the sequencing reactions, it was determined which of the FSTs co-segregate as homozygous with the stf phenotype. Out of 41 FSTs analyzed from line NF0075 (stf1-1), only NF0075-insert 2 (FST2) was found in all six lines and the Tnt1 insert at this locus segregated with stf as homozygous every time (FIG. 5). The NF0075-FST2-specific primers used in FIG. 5 amplify ~700 by fragment in wild-type R108. All the wild-type (R108)-looking plants in the segregating population amplify this band (FIG. 5 right panel) showing that they are either homozygous wild-type (no additional band), or heterozygous for the Tnt1 insertion (having a second upper band). All plants with the stf phenotype on the other hand amplify only the upper band (FIG. 5 left panel) which corresponds to the 700 by fragment plus the complete 5.3 kb Tnt1 element. This co-segregation of the 6 kb PCR™ band and the stf phenotype demonstrates that all of the segregating stf mutants contain a homozygous Tnt1 insertion in their genome at the FST 2 locus. Similarly, it was confirmed that the plants with the stf phenotypes in the other 5 independent lines also contain homozygous Tnt1 insertions at the FST2 locus. It was concluded that Tnt1 insertion at this FST2 locus is responsible for the stf phenotype and that the six independent stf lines are allelic. A BLAST search of the *Medicago* genome showed that FST2 corresponds to part of a gene predicted to be a homeobox transcription factor.

Figure 6A:
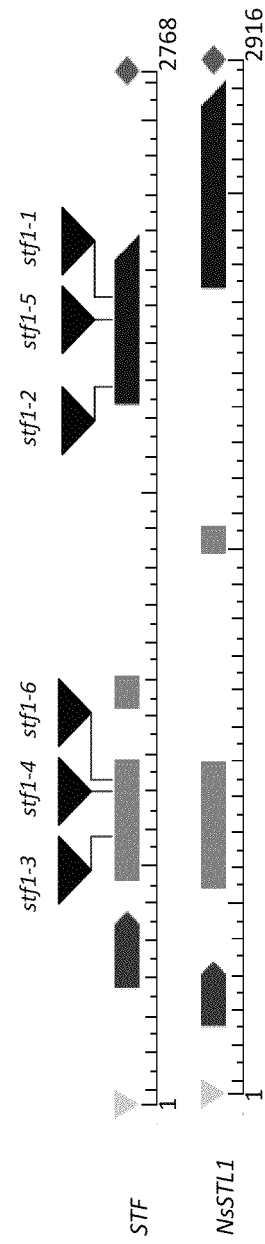
Figure 6B:
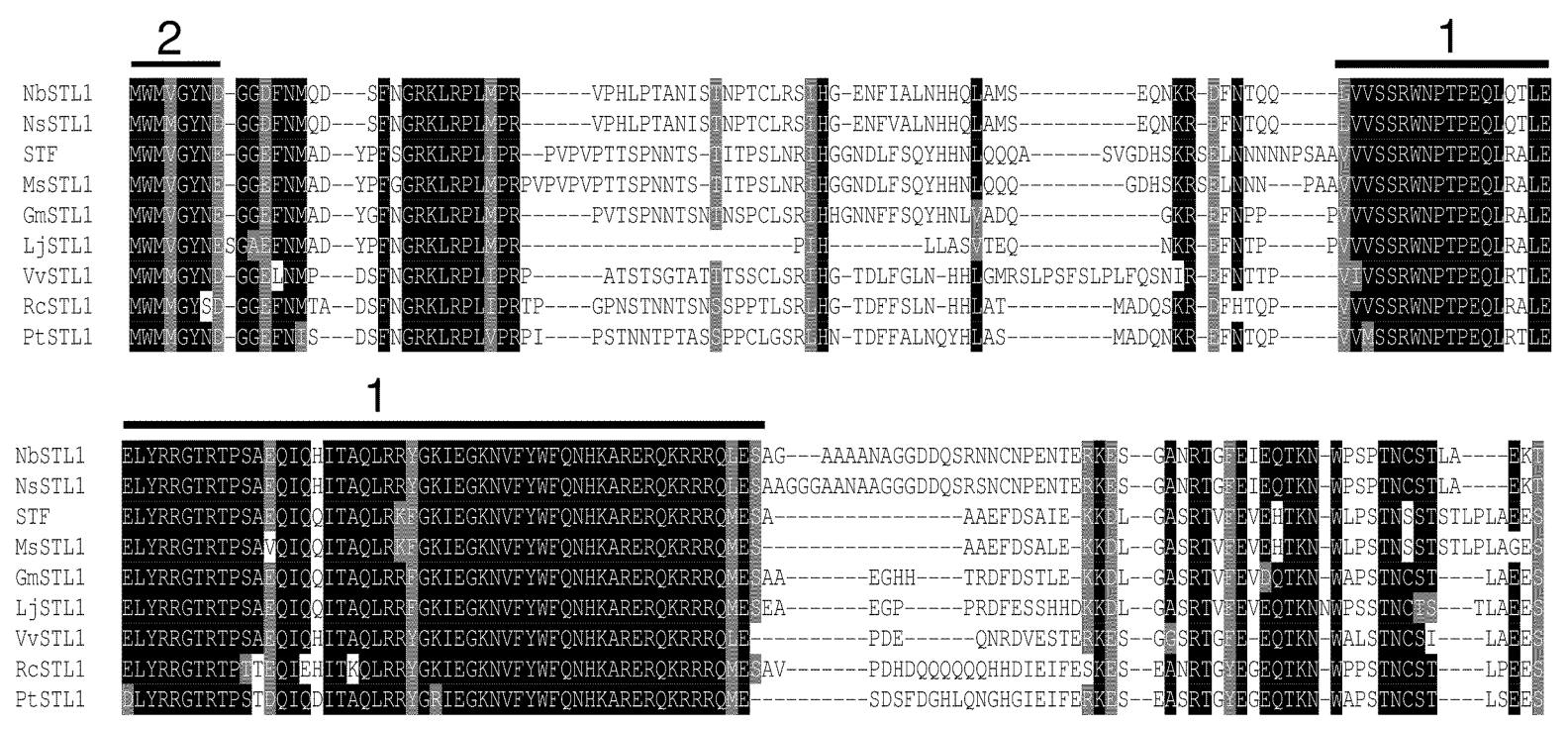
Figure 6B:
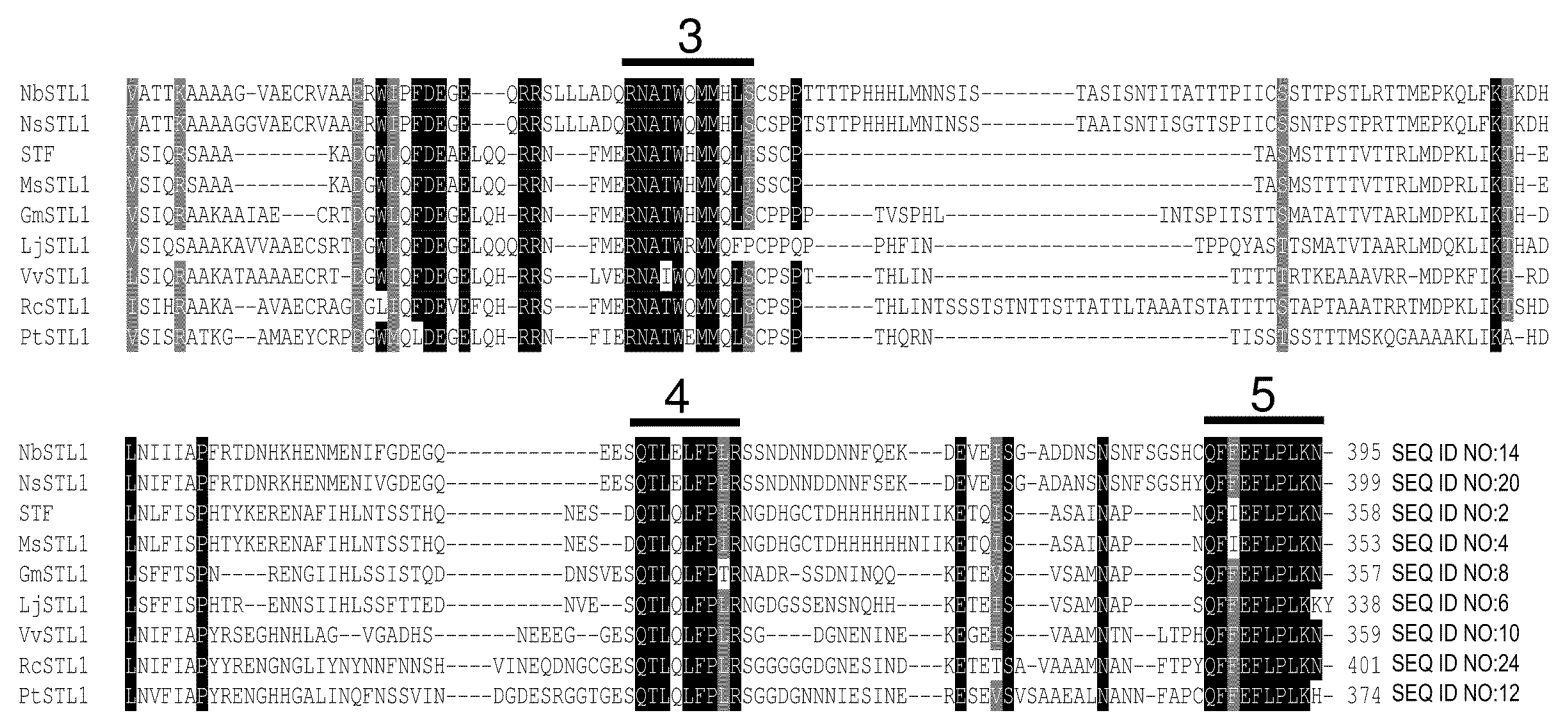
Figure 6C:
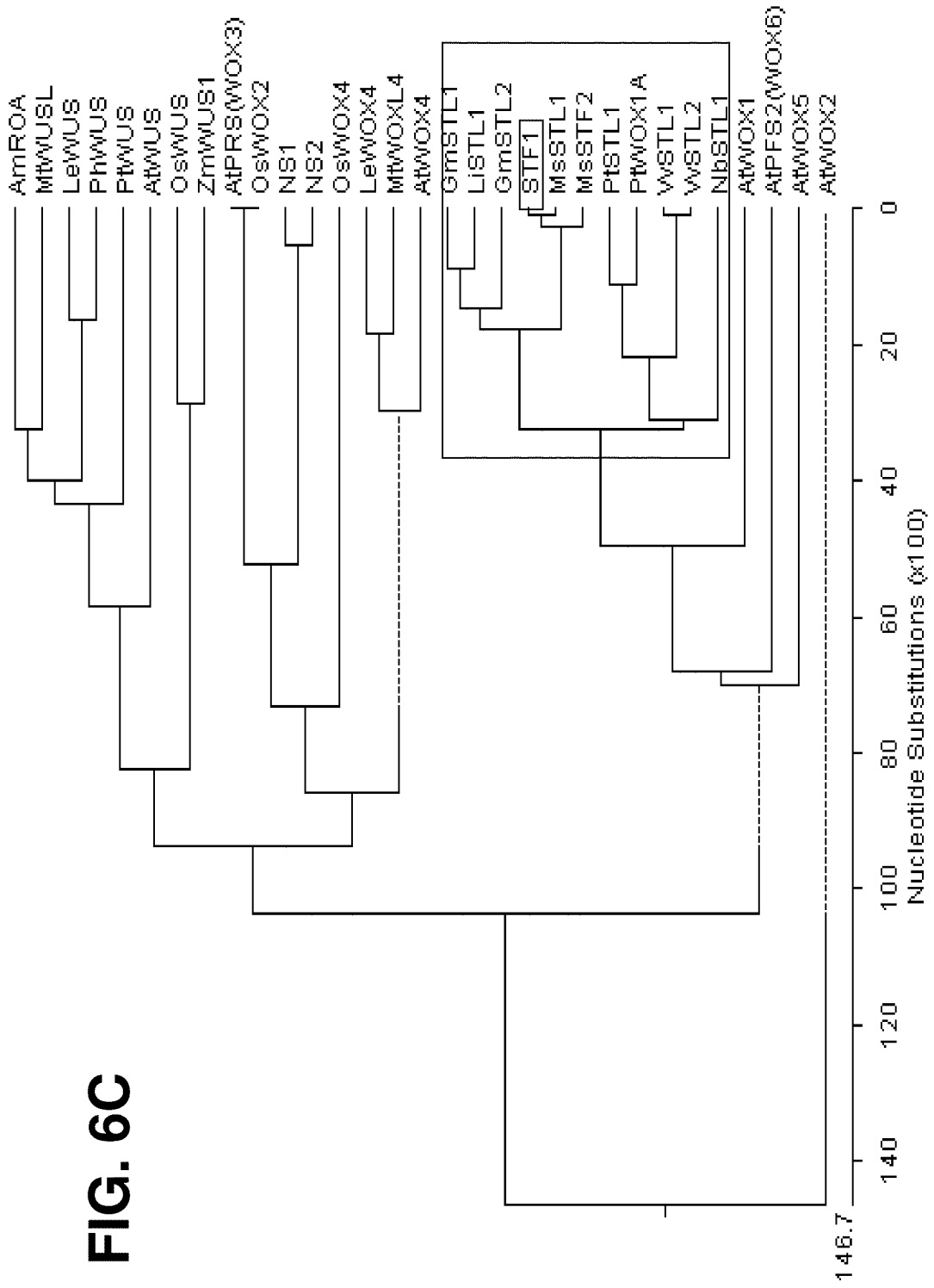

The full-length cDNA of the gene at the FST2 locus was cloned from genotype R108 by RT-PCR, and a full-length genomic sequence based on the A17 genome sequence was identified. This gene is hereafter designated as STF. STF is 2.7 kb in length from transcription start to poly A with four exons (FIG. 6A). When this gene was analyzed in plants from each of the six lines with the stf phenotype, each of the six lines had a stf allele with a Tnt1 insertion at a different location within an exon. BLAST homology searching and analysis shows that STF belongs to the WOX class of transcription factors and encodes a putative homeodomain protein of 358 amino acids. The closest *Arabidopsis* homologue is WOX1 with 38% overall amino acid identity, but putative orthologues with stronger homology were isolated from alfalfa, lotus, soybean, grape, poplar and tobacco by a homology searching strategy and RT-PCR based on the STF sequence. These clones from other species were named STL for STF-like as their functions were not immediately analyzed. However, STF and STL proteins share at least four more highly conserved motifs in addition to the homeodomain; one at the 5' region, one at the 3' very end and two between the homeodomain and the 3' end (FIG. 6B). Neighbor joining phylogenetic analysis suggests that STF and the sequences identified as orthologues probably belong to a new sub-clade of WOX-like proteins separate from WOX1 and other homeodomain proteins described to date (FIG. 6C).

There are 15 of WOX-like genes in *Arabidopsis*, including the founding member WUSCHEL (Haecker et al., 2004), but none of them is implicated specifically in leaf lamina development. The maize narrow sheath (ns1/ns2) double mutants show a lamina deletion phenotype (Nardmann et al., 2004) and the NS1 and NS2 genes are related to the *Arabidopsis* WOX gene PRESSED FLOWER (PRS/WOX3). prs mutants are affected in lateral sepals, lateral stamens, and stipule formation but not in leaf lamina expansion (Matsumoto and Okada, 2001; Nardmann et al., 2004). In *Arabidopsis*, WOX1 expression is confined to the initiating vascular primordia of the cotyledons in heart and torpedo stage embryos, and wox1 insertional mutants have no obvious phenotype (Haecker et al., 2004). This suggests that STF represents a new subclass of WOX-related genes with a key role in lateral expansion and adaxial cell fate specification.

STF is expressed at very low background levels. Induction of expression was detected by qPCR in the shoot apex, flower, and developing pod. To determine the location of specific expression in the shoot apex and flower, in situ hybridization was performed using a 3'-end STF-specific fragment as a probe. STF is weakly expressed in most cells of the leaf primordia. In the incipient, P1, and P2 primordia, STF is adaxially expressed in a few cells but absent from the rest of the shoot apical meristem (SAM) (FIG. 7A). In older primordia, expression extends to a few more cells and moves towards the central region while still in the adaxial side. This is consistent with the observed function of STF being required for adaxial identity. FIG. 7B shows a negative control with a sense probe. STF expression in the floral primordia is even weaker than in the leaf primordia but has a wider expression domain (FIG. 7C). FIG. 7D shows a positive control for floral organs with expression of the PIM (homologue of AP1) gene.

Although the stf mutant phenotype and the STF expression pattern are consistent with STF being a key adaxializing factor, they do not show how STF exerts its effects. As STF is a predicted transcription factor, it can be anticipated to alter the expression profile of other genes downstream. However, there were no immediate candidate genes to look for as this gene has not been studied in other species and polarity genes have not been characterized in *M. truncatula*. Therefore a comprehensive approach was taken to look for alteration of global gene expression between the stf mutants and the segregating progeny using the 52k Affymetrix chips of *M. truncatula*. RNA for this analysis was extracted from 4 weeks old shoot apices pooled from more than 10 plants of stf and wild-type looking segregating individuals. Three independent stf alleles were used as biological replicates. This strategy eliminates any background noise that might be caused by Tnt1 insertion in other genes.

A total of 106 genes were identified as down-regulated and 136 genes as up-regulated in the mutant, when a change in expression was assessed using a 2-fold change in expression as the cut off. Interestingly, KNAT2, AUXIN INDUCED PROTEIN, and ARF3 like genes are among the most-highly up regulated genes, and SCR, TCP, ENT KAURENOIC ACID OXIDASE, and AUXIN EFFLUX CARRIER like genes are among the most-strongly down regulated genes. The up-regulation of a KNAT2-like gene in the mutant suggests that STF also interacts with KNOX genes to prevent their expression in primordia. Without being bound by theory, these results are consistent with the function of STF as determinant of adaxial cell fate.

Example 3

Identification and Characterization of the lam1 Mutant of *Nicotiana sylvestris*

The lam1 mutant of *Nicotiana sylvestris* displays phenotypes that strongly resembled stf except that lam1 phenotypes are stronger with conspicuous absence of stems (FIG. 8A, B). From morphological analysis of mutant phenotypes it was considered that stf and lam1 may be caused by mutations in homologous genes.

To test this, an STF-like gene (NsSTL1) from wild-type *N. sylvestris* was cloned by PCR using the STF sequence to design primers. NsSTL1 is similar to STF in gene structure, having four exons and comparable exon sizes (FIG. 6A). NsSTL1 encodes a predicted 374 amino acid protein which shares 45% amino acid identity overall with STF. An attempt was then made to PCR-amplify the NsSTL1 gene in the lam1 mutant to identify the mutation, revealing that NsSTL1 was deleted. Various primer combinations specific to NsSTL1 including 2.46 kb region of the promoter and 3' UTR detected no amplification in the mutant compared to wild-type (FIG. 8C, D). It was concluded that at least a 5.67 kb region of the NsSTL1 locus is deleted in the lam1 mutant.

To confirm that the lam1 mutant is deficient in NsSTL function, a 5.3 kb genomic fragment of STF from *M. truncatula* was introduced into the lam1 mutant via *Agrobacterium*-mediated transformation, and plants were regenerated through somatic embryogenesis. The *Medicago* STF gene fully complemented lam1 (FIG. 8E), confirming that STF function is indeed absent in the lam1 mutant and that STF and LAM1 are orthologs. The complemented lam1 plants were indistinguishable from the wild-type except that approximately 5% of the complemented lam1 plants produced leaves that were 5-20% broader than the wild-type.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. Nos. 4,535,060; 5,302,523; 5,322,783; 5,384,253; 5,464,765; 5,508,184 5,538,877; 5,538,880; 5,545,818; 5,550,318; 5,563,055; 5,591,616; 5,610,042

Abdullah et al., *Biotechnology* 4:1087, 1986.
Altschul et al., *J. Mol. Biol.* 215:403-410, 1990.
Barton and Poethig, *Development* 119: 823-831, 1993.
Bates, *Mol. Biotechnol.* 2(2):135-145, 1994.
Battraw and Hall, *Theor. App. Genet.* 82(2):161-168, 1991.
Bendtsen et al., *J. Mol. Biol.* 340:783-795, 2004.
Bevan et al., *Nucleic Acids Research* 11(2):369-385, 1983.
Bhattacharjee et al., *J. Plant Bioch. Biotech.* 6, (2):69-73. 1997.
Biocomputing: Informatics and Genome Projects, Smith (Ed.), Academic Press, NY, 1993.
Birren, et al., *Genome Analysis* 1:543-559, 1997.
BLAST Manual, Altschul et al. (Eds.), NCBI NLM NIH, Bethesda, Md. 20894
Bower et al., *Plant J.* 2:409-416. 1992.
Buising and Benbow, *Mol Gen Genet* 243(1):71-81. 1994.
Byrne, M. E., *PLoS Genet* 2: e89, 2006.
Callis et al., *Genes Dev.* 1:1183-1200, 1987.
Carillo and Lipman, SIAM *J. Applied Math* 48:1073, 1988.
Casa et al., *Proc. Natl. Acad. Sci. USA* 90(23):11212-11216, 1993.
Chandler et al., *Plant Cell* 1:1175-1183, 1989.
Chen et al., *Biotechniques* 16:664-670, 1994.
Chiu et al., *Curr. Biol.* 6:325-330, 1996.
Chu et al., *Scientia Sinica* 18:659-668, 1975.
Chuck et al., *Plant Cell* 8:1277-1289, 1996.
Clark et al., *Cell* 89: 575-585, 1997.
Clough and Bent, *Plant J.* 16:735-743, 1998.
Computational Molecular Biology, Lesk (Ed.), Oxford University Press, NY, 1988.
Computer Analysis of Sequence Data, Part I, Griffin and Griffin (Eds.), Humana Press, NJ, 1994.
Conkling et al., *Plant Physiol.* 93:1203-1211, 1990.
Coulson, *Trends Biotech.* 12:76-80, 1994.
DE 3642 829
De Block et al., *EMBO J.* 6(9):2513-2518, 1987.
De Block et al., *Plant Physiol.* 91:694-701, 1989.
Dellaporta et al., *In: Chromosome Structure and Function: Impact of New Concepts,* 18th Stadler Genetics Symposium, 11:263-282, 1988.
Devereux et al., *Nucleic Acids Res.* 12(1):387, 1984.
Doerner, *Current Biology* 13: R368-R374, 2003.
Downward, *BMJ* 328(7450):1245-1248, 2004.
Ebert et al., *Proc. Natl. Acad. Sci. USA* 84:5745-5749, 1987.
Emanuelsson et al., *J. Mol. Biol.* 300:1005-1016, 2000.
Emery et al., *Curr Biol* 13: 1768-1774, 2003.
EPA App. 154,204
Eshed et al., *Curr Biol* 11: 1251-1260, 2001.
Eshed et al., *Development* 131: 2997-3006, 2004.
Fire et al., *Nature* 391(6669):806-811, 1998.
Fletcher et al., *Science* 283: 1911-1914, 1999.
Fraley et al., *Bio/Technology* 3:629-635, 1985.
Fromm et al., *Nature* 319:791-793, 1986.
Gallie et al., *Plant Cell* 1:301-311, 1989.
Gaston et al., *J. Environ. Qual.* 32:1422-1429, 2003.
Gelvin et al., *In: Plant Molecular Biology Manual,* 1990.
Ghosh-Biswas et al., *J. Biotechnol.* 32(1):1-10, 1994.
Hagio et al., *Plant Cell Rep.* 10(5):260-264, 1991.
Haecker et al., *Development* 131: 657-668, 2004.
Haseloff et al., *Proc. Natl. Acad. Sci. USA* 94(6):2122-2127, 1997.
He et al., *Plant Cell Reports* 14 (2-3):192-196, 1994.
Hensgens et al., *Plant Mol. Biol.* 22(6):1101-1127, 1993.
Hentikoff and Hentikoff, *Proc. Natl. Acad. Sci USA* 89:10915-10919, 1992.
Hiei et al., *Plant Mol. Biol.* 35(1-2):205-218, 1997.
Hinchee et al., *BioTechnol.* 6:915-922, 1988.
Hudspeth and Grula, *Plant Mol. Biol.* 12:579-589, 1989.
Ikuta et al., *BioTechnol.* 8:241-242, 1990.
Ishidia et al., *Nat. Biotechnol.* 14(6):745-750, 1996.
Iwakawa et al., *Plant Cell Physiol.* 43: 467-478, 2002.
Jeong et al., *Plant Cell* 11: 1925-1934, 1999.
Kaeppler et al., *Plant Cell Reports* 9:415-418, 1990.
Kaeppler et al., *Theor. Appl. Genet.* 84(5-6):560-566, 1992.
Katz et al., *J. Gen. Microbiol.* 129:2703-2714, 1983.
Klee et al., *BioTechnology* 3(7):637-642, 1985.
Knittel et al., *Plant Cell Reports* 14(2-3):81-86, 1994.
Lawton et al., *Plant Mol. Biol.* 9:315-324, 1987.
Laux et al., *Development* 122: 87-96, 1996.
Lazzeri, *Methods Mol. Biol.* 49:95-106, 1995.
Lehner et al., *Brief Funct. Genomic Proteomic.* 3(1):68-83, 2004.
Lin et al., *Plant Cell* 15: 2241-2252, 2003.
Liu et al., *Mol. Plant Microbe Interact.* 11(1):14-22, 1998.
Long et al., *Nature* 379: 66-69, 1996.
Mallory et al., *EMBO J.* 23: 3356-3364, 2004.
Matsumoto and Okada, *Genes Dev.* 15: 3355-3364, 2001.
Mayer et al., *Cell* 95: 805-815, 1998.
McCabe and Martinell, *BioTechnology* 11(5):596-598, 1993.
McConnell et al., *Nature* 411: 709-713, 2001.
McCormac et al., *Euphytica* 99(1):17-25, 1998.
McHale, *Planta* 186: 355-360, 1992.
McHale and Koning, *Plant Cell* 16: 1730-1740, 2004.
McHale and Marcotrigiano, *Development* 125: 4235-4243, 1998.
Mihaliak et al., *Meth. Plant Biochem.* 9:261-279, 1993.
Murakami et al., *Mol. Gen. Genet.* 205:42-50, 1986.
Murashige and Skoog, *Physiol. Plant.* 15:473-497, 1962.
Murphy and Riley, *Anal. Chim. Acta* 27:31-36, 1962.
Nagatani et al., *Biotech. Tech.* 11(7):471-473, 1997.
Nardmann et al., 131: 2827-2839, 2004.
Needleman and Wunsch, *J. Mol. Biol.* 48:443-453, 1970.
Nielsen et al., *Protein Eng.* 10:1-6, 1997.
Nielsen, *Nat. Biotechnol.* 21(3):227-228, 2003.
Odell et al., *Nature* 313:810-812, 1985.
Ogawa et al., *Sci. Rep.* 13:42-48, 1973.
Olah and Sherwood, *Phytopathology* 61:65-69, 1971.
Omirulleh et al., *Plant Mol. Biol.* 21(3):415-428, 1993.
Otsuga et al., *Plant J* 25: 223-236, 2001.
Ow et al., *Science* 234:856-859, 1986.
PCT Appln. WO 92/17598
PCT Appln. WO 94/09699
PCT Appln. WO 95/06128
PCT Appln. WO 97/04103
PCT Appln. WO 97/41228
Pote et al., *J. Environ. Qual.* 32:2392-2398, 2003.
Potrykus et al., *Mol. Gen. Genet.* 199:183-188, 1985.
Prasher et al., *Biochem. Biophys. Res. Commun.* 126(3): 1259-1268, 1985.
Reichel et al., *Proc. Natl. Acad. Sci. USA,* 93(12):5888-5893, 1996.
Ritala et al., *Plant Mol. Biol.* 24(2):317-325, 1994.
Rogers et al., *Methods Enzymol.* 153:253-277, 1987.
Rommens et al., *Plant Physiol.* 135:421-431, 2004.
Sambrook et al., *In: Molecular cloning: a laboratory manual,* $2^{nd}$ Ed., Cold Spring Harbor Laboratory, NY, 1989.
Schumacher et al., *Plant Cell Rep.* 6:410-413, 1987.
Sequence Analysis in Molecular Biology, von Heinje (Ed.), Academic Press, NY, 1987.

Sequence Analysis Primer, Gribskov and Devereux (Eds.), Stockton Press, NY, 1991.
Sheen et al., *Plant J.* 8(5):777-784, 1995.
Singsit et al., *Transgenic Res.* 6(2):169-176, 1997.
Stalker et al., *Science* 242:419-422, 1988.
Sullivan et al., *Mol. Gen. Genet.* 215(3):431-440, 1989.
Sutcliffe, *Proc. Natl. Acad. Sci. USA* 75:3737-3741, 1978.
Tang et al., *Genes Dev.* 17: 49-63, 2003.
Thomas et al., *Plant Sci.* 69:189-198, 1990.
Thompson et al., *EMBO J.* 6(9):2519-2523, 1987.
Thompson et al., *Euphytica* 85(1-3):75-80, 1995.
Tian et al., *Plant Cell Rep.* 16:267-271, 1997.
Tingay et al., *Plant J.* 11(6):1369-1376, 1997.
Tomes et al., *Plant. Mol. Biol.* 14(2):261-268, 1990.
Torbet et al., *Crop Science* 38(1):226-231, 1998.
Torbet et al., *Plant Cell Reports* 14(10):635-640, 1995.
Toriyama et al., *Theor Appl. Genet.* 73:16, 1986.
Trotochaud et al., *Science* 289: 613-617, 2000.
Tsukada et al., *Plant Cell Physiol.* 30(4)599-604, 1989.
Tsukaya, *Int J Dev Biol* 49: 547-555, 2005.
Twell et al., *Plant Physiol.* 91:1270-1274, 1989.
Van Eck et al., *Plant Cell Reports* 14(5):299-304, 1995.
Vasil et al., *Plant Physiol.* 91:1575-1579, 1989.
Vogel et al., *Arch. Biochem. Biophys.* 401:164-172, 2002.
Vollbrecht et al., *Nature* 350: 241-243, 1991.
Walker et al., *Proc. Natl. Acad. Sci. USA,* 84:6624-6628, 1987.
Wang et al., *Molec. Cell. Biol.* 12(8):3399-3406, 1992.
Waites and Hudson, *Development* 121: 2143-2154, 1995.
Waites et al., *Cell* 93: 779-789, 1998.
Xu et al., *Cell Res* 17: 512-519, 2007.
Xu et al., *Development* 130: 4097-4107, 2003.
Xu et al., *Acta Bot Sin* 44: 1194-1202, 2002.
Yamada et al., *Plant Cell Rep.* 4:85, 1986.
Yang and Russell, *Proc. Natl. Acad. Sci. USA* 87:4144-4148, 1990.
Yu et al., *New Phytol.* 143:299-304, 1999.
Zheng and Edwards, *J. Gen. Virol.* 71:1865-1868, 1990.
Zhong and Ye, *Plant Cell Physiol.* 45: 369-385, 2004.
Zukowsky et al., *Proc. Natl. Acad. Sci. USA* 80:1101-1105, 1983.

What is claimed is:

1. A recombinant vector comprising a nucleic acid sequence selected from the group consisting of:
   (a) a sequence encoding a polypeptide at least 85% identical to SEQ ID NO:2;
   (b) a sequence comprising SEQ ID NO:1;
   (c) a sequence comprising at least 85% sequence identity over the full length of SEQ ID NO:1; and
   (d) a sequence fully complementary to (a), (b), or (c),
   wherein the sequence of (a), (b), or (c) confers altered biomass in a plant transformed therewith, and wherein the nucleic acid is operably linked to a heterologous promoter functional in plants.

2. The recombinant vector of claim 1, further comprising at least one additional sequence chosen from the group consisting of: a regulatory sequence, a selectable marker, a leader sequence and a terminator.

3. The recombinant vector of claim 2, wherein the additional sequence is a heterologous sequence.

4. The recombinant vector of claim 1, wherein the promoter is a tissue-specific promoter.

5. The recombinant vector of claim 1, wherein the promoter directs expression in leaf primordia.

6. The recombinant vector of claim 1, defined as an isolated expression cassette.

7. A transgenic plant transformed with the recombinant vector of claim 1.

8. The transgenic plant of claim 7, further defined as a dicotyledonous plant.

9. The transgenic plant of claim 7, further defined as a poplar, a willow, a eucalyptus, a hemp, a *Medicago* sp., a *Lotus* sp., a *Trifolium* sp., a *Melilotus* sp., a *Vinca* sp., a *Glycine* sp., a *Nicotiana* sp., a *Vitis* sp., or a *Ricinus* sp.

10. The transgenic plant of claim 7, further defined as an $R_0$ transgenic plant.

11. The transgenic plant of claim 7, further defined as a progeny plant of any generation of an $R_0$ transgenic plant, wherein the transgenic progeny plant has the nucleic acid molecule from the $R_0$ transgenic plant comprising the recombinant vector of claim 5.

12. A seed of the transgenic plant of claim 7, wherein the seed comprises the nucleic acid molecule.

13. A plant or bacterial host cell transformed with the recombinant vector of claim 1.

14. The host cell of claim 13, wherein said host cell is a plant cell.

15. A method of altering biomass in a plant, the method comprising expressing in the plant the recombinant vector according to claim 1, wherein the expression of the nucleic acid molecule alters the biomass of the plant when compared to a plant of the same genotype that lacks the nucleic acid molecule.

16. The method of claim 15, wherein the plant is an $R_0$ transgenic plant.

17. The method of claim 15, wherein the plant is a progeny plant of any generation of an $R_0$ transgenic plant, wherein the transgenic plant has the nucleic acid molecule from the $R_0$ transgenic plant.

18. The method of claim 15, wherein the altered biomass is increased biomass.

19. The method of claim 15, wherein the plant has altered morphology when compared to a plant of the same genotype that lacks the nucleic acid molecule.

20. The method of claim 19, wherein the altered morphology is altered leaf morphology.

21. A method of producing plant biomass, the method comprising:
   (a) obtaining the plant of claim 7;
   (b) growing said plant under plant growth conditions to produce plant tissue from the plant; and
   (c) preparing biomass from said plant tissue.

22. The method of claim 21, wherein preparing biomass comprises harvesting said plant tissue.

23. The method of claim 21, further comprising using the biomass for biofuel.

24. The recombinant vector of claim 1, comprising SEQ ID NO:1.

* * * * *